United States Patent
Dutta et al.

(10) Patent No.: US 9,420,941 B2
(45) Date of Patent: Aug. 23, 2016

(54) IMAGE DETECTING CAPSULE DEVICE AND MANUFACTURING THEREOF

(71) Applicant: Banpil Photonics, Inc., Santa Clara, CA (US)

(72) Inventors: Achyut Dutta, Sunnyvale, CA (US); Robert Olah, Sunnyvale, CA (US)

(73) Assignee: Banpil Photonics, Inc., Santa Clara, CA (US)

( * ) Notice: Subject to any disclaimer, the term of this patent is extended or adjusted under 35 U.S.C. 154(b) by 394 days.

(21) Appl. No.: 13/831,812

(22) Filed: Mar. 15, 2013

(65) Prior Publication Data
US 2014/0275776 A1    Sep. 18, 2014

(51) Int. Cl.
*A61B 1/04* (2006.01)
*A61B 1/00* (2006.01)

(52) U.S. Cl.
CPC ........... *A61B 1/041* (2013.01); *A61B 1/00029* (2013.01); *A61B 1/00032* (2013.01); *A61B 1/00034* (2013.01); *A61B 1/00025* (2013.01); *A61B 2560/0214* (2013.01)

(58) Field of Classification Search
CPC .......... A61B 1/00025; A61B 1/00027; A61B 1/00029; A61B 1/00032; A61B 1/00034; A61B 1/041; A61B 2560/0214; A61B 2560/0219
See application file for complete search history.

(56) References Cited

U.S. PATENT DOCUMENTS

| | | | | |
|---|---|---|---|---|
| 4,403,826 A | * | 9/1983 | Presby | 385/141 |
| 4,686,373 A | * | 8/1987 | Tew et al. | 348/164 |
| 4,844,076 A | * | 7/1989 | Lesho | A01K 11/007 |
| | | | | 128/903 |
| 4,910,154 A | * | 3/1990 | Zanio et al. | 438/60 |
| 5,047,947 A | * | 9/1991 | Stump | 700/106 |
| 5,833,603 A | * | 11/1998 | Kovacs et al. | 600/317 |
| 7,044,908 B1 | * | 5/2006 | Montalbo | A61B 1/00183 |
| | | | | 600/109 |
| 7,501,726 B1 | * | 3/2009 | Waters et al. | 310/36 |
| 8,823,210 B1 | * | 9/2014 | Olah | H02J 7/0055 |
| | | | | 307/45 |
| 2004/0249245 A1 | * | 12/2004 | Irion | A61B 1/041 |
| | | | | 600/160 |
| 2005/0228259 A1 | * | 10/2005 | Glukhovsky et al. | 600/407 |
| 2005/0270664 A1 | * | 12/2005 | Pauker et al. | 359/694 |
| 2006/0264702 A1 | * | 11/2006 | Ishibashi | A61B 1/00016 |
| | | | | 600/101 |
| 2007/0204901 A1 | * | 9/2007 | Dutta | 136/256 |
| 2007/0263293 A1 | * | 11/2007 | Batchko et al. | 359/666 |
| 2007/0282165 A1 | * | 12/2007 | Hopkins et al. | 600/109 |
| 2008/0033569 A1 | * | 2/2008 | Ferren et al. | 623/23.7 |
| 2008/0210872 A1 | * | 9/2008 | Grimberg | G01J 5/522 |
| | | | | 250/339.04 |
| 2008/0245407 A1 | * | 10/2008 | Jackson | H02S 99/00 |
| | | | | 136/253 |
| 2008/0306360 A1 | * | 12/2008 | Robertson et al. | 600/302 |
| 2009/0326323 A1 | * | 12/2009 | Uchiyama et al. | 600/118 |
| 2010/0030025 A1 | * | 2/2010 | Segawa et al. | 600/118 |

(Continued)

FOREIGN PATENT DOCUMENTS

JP     2001231187 A  *  8/2001 ............. H02J 17/00
WO  WO 2012003529 A1 *  1/2012

*Primary Examiner* — John P Leubecker

(57) ABSTRACT

Autonomous/self-powering image detecting systems and their manufacturing technologies are disclosed. An antenna is used to communicate signals. A first energy harvester is used to harvest energy from blackbody radiation, RF signals, movement/vibration, or combination thereof. A power management system is used which controls the energy flow to and from the energy-storage. An image sensor to take the image, a lens, and a transmitter to transmit the images to an outside device are also used in this invention. According to this preferred embodiment, an energy harvester harnessing energy from blackbody radiation from and within the body, is used to extract enough energy to increase the operation time and also to make precision of the image detecting system.

16 Claims, 30 Drawing Sheets

(56) References Cited

U.S. PATENT DOCUMENTS

| | | | |
|---|---|---|---|
| 2011/0115891 A1* | 5/2011 | Trusty | 348/65 |
| 2011/0144573 A1* | 6/2011 | Rofougaran et al. | 604/66 |
| 2011/0285835 A1* | 11/2011 | Koide | A61B 1/00016 348/76 |
| 2012/0004523 A1* | 1/2012 | Richter et al. | 600/345 |
| 2012/0298190 A1* | 11/2012 | Dutta | H01L 31/022425 136/253 |
| 2013/0114149 A1* | 5/2013 | Michael et al. | 359/696 |
| 2014/0366927 A1* | 12/2014 | Lavrova et al. | 136/244 |
| 2015/0035378 A1* | 2/2015 | Calhoun et al. | 307/104 |

\* cited by examiner $$W(\lambda) = \frac{c_1}{\lambda^5(e^{c_2/\lambda T} - 1)}$$

$c_1 = 2\pi c^2 h = 37418.32\ w\mu^4 cm^{-2}$ $c_2 = hc/k = 14387.86\ \mu K$

C : Speed of light
k: Boltzman's constant
h: Planck's constant
λ: Lamda-wavelength
T: Temperature in Kelvin

FIG. 2A

IMAGE DETECTING CAPSULE DEVICE AND MANUFACTURING THEREOF

FIELD OF THE INVENTION

This invention is directed to the field of miniaturized wireless biopill for endoscopy imaging. More particularly, this invention is related to small form-factor endoscopic capsule system for increased performance by employing the use of perpetual energy sources using the body heat source.

BACKGROUND OF THE INVENTION

The contents of all references, including articles, published patent applications and patents, if referred to anywhere in this specification are hereby incorporated by reference.

FIG. 1 shows a schematic showing cross-sectional view of human's gastrointestinal (GI) system (from mouth to rectum). Diagnosis of disease in whole GI tract is very limited using today's invasive endoscopic technique. Diagnosis of problems in the small intestine has been very difficult. Push endoscopy is the most widely used method of observing issues in the small intestine. Push endoscopy is a procedure in which an endoscope is pushed through the mouth through the upper gastrointestinal (GI) tract into the small intestine. Only between 120 and 150 cm of the small intestine can be examined with this method. The small intestine is between 3.75 to 8.25 meters so only a portion of the intestine can be observed. Most of the deep intestinal issues or problems are undiagnosed using standard endoscopy. In addition, standard technique is not only painful to patient, but also it takes longer time going through whole diagnosis procedure based on this standard endoscopy method. It is highly desirable to have a method which is takes less or no time for patient in diagnosis procedure.

Recently, wireless video capsules have been developed to be able to observe the small intestine by taking and transmitting pictures as the capsule is passed through the small intestine. The capsules usually have an optical dome, lens, illuminating LEDs, CMOS focal array, batteries, electronics, wireless transmitter. The small capsule (the PillCam small bowel (SB) M2A, GIVEN Imaging Inc.) measured 26 mm in length and 11 mm in diameter. Similar size capsule, named EndoCapsule, marketed by Olympus later is clinically approved. The capsule, when ingested, will travel down the esophagus through the stomach and through the small intestine. The battery will last about 6 to 8 hours taking two pictures per second. Pictures are wirelessly transmitted to a data recorder that is attached to a belt around the waist. The capsule moves too quickly through the esophagus to take enough pictures at 2 pictures per second. The capsule also cannot take pictures of a large part of the stomach. The battery will run out before entering the large intestine so the large intestine will also not be observed. Rate of transmission through the small intestine will depend on the individual patient. A rate too fast beyond 2-3 cm/sec with the current rate of 2 sec/frame could result in missed detail.

Longer battery life could allow the capsule to take (i) more pictures at (ii) a faster rate and (iii) to last longer also (iv) to observe the large intestine. Battery capacity is related to battery technology and size. Present battery technology that will fit into the capsule is limited to about 60 ma-h. This is a major limitation of making the capsule more universally accepted. Because of the limitation on battery life, many approaches for slowing down or strategically stopping the capsule for more detailed images are infeasible. Slower or more controlled mobility would allow more observation down the esophagus and more time controlled in the stomach. All this additional information is collected taking additional time that is not available based on current battery life.

With extended energy capability there is then no limitation to the time spent stopping and viewing specific areas to better diagnose internal issues. With more energy available some of the disadvantages of the capsule can be overcome and more feature could be incorporated into the capsule. For example, features (i) to take more high resolution images, (ii) to retrieve tissue from suspicious areas, (iii) to collect fluid samples and (iv) perform cytology brushing could be added. All these additional features require additional power supply. With that need in mind, this invention is a wireless ingestible capsule which employs use of rechargeable energy sources and/or energy generating sources. The most importantly, with incorporating the energy generation source is not only replace the battery, as a major power supply, but it also provides more advantages to make the capsule more small form-factor, even if it needs a small battery, medically friendly to all ages of patient.

SUMMARY OF THE INVENTION

According to an embodiment of the current invention, endoscopic system is an wireless operatable image sensing capsule with an integrated energy harvester, that includes three mains sections: at least one battery, section of imaging components, and a section of power harvesting, power management, and image transmission.

As explained in greater detail below, however, some components may be moved to different locations or omitted completely. For example, in some embodiments the battery is eliminated, allowing greater flexibility for placement of the remaining components and reduction of size for the entire capsule.

According to an embodiment of this current invention, an endoscope system that is an wireless rechargeable imaging capsule, comprises at least one energy harvester, a image sensor array, at least one lens, a wireless transmitter, an antenna, and a power management unit. According to this invention, the harvester of endoscope system harvest the energy from blackbody, and in this case human body heat (e.g. adult .about.36.5 C) and/or from the body-vibration, from RF signal, if any, or some combination thereof, and supply to other optoelectronics components for image capturing, processing, and transmission. The image sensor array can be built and configured to sense light from the visible spectrum up to the mid-infrared spectrum. One lens should be placed so that it concentrates light in the desired image spectrum on the image sensor array. If the energy harvester is of a type which absorbs blackbody radiation, then an additional lens may be used to concentrate the radiation on the harvester.

According to this invention, the image sensor array could be CMOS based Si image sensor, and or image sensor that can capture the image from within Visible (VIS) to Midwave Infrared (MWIR), or within VIS to Longwave Infrared (LWIR). If CMOS image sensor is used, visible light emitter is needed to incorporate. According to this invention for other image sensor, light emitter may or may not necessary. According to this invention, the energy harvester and image sensor are also integrated monolithically or hybridly which yet to make the whole endoscopy system more compact and less power consumption.

According to another embodiment of this current invention, the endoscope system includes, includes at least one battery or capacitor, a image sensor array, a light emitter, at least one lens, a wireless transmitter, an antenna, an energy harvesting unit, and a power management unit. The image sensor array can be built and configured to sense light from the visible spectrum up to the mid-infrared spectrum. The energy harvesting unit can be based on absorption of blackbody radiation, absorption of vibrations, absorption of heat, absorption from RF signals, or some combination thereof. One lens should be placed so that it concentrates light in the desired image spectrum on the image sensor array. If the energy harvester is of a type which absorbs blackbody radiation, then an additional lens can be used to concentrate the radiation on the harvester.

Alternatively, if the image sensor array is built and configured to sense light outside the visible spectrum, like from near visible to mid-infrared, then the battery and LEDs can be omitted. The energy harvested can all be used to run the components alone.

Alternatively, if the image sensor is built and configured to sense light in a broad spectrum, including visible light and non-visible, then at least one light source s can be used, and therefore a small battery may be used. The battery could be power supply and also restored the energy from energy harvester.

According to the invention, the energy harvesting unit can be a single pixel or an array. Additionally, it may be placed either in the rounded section of the pill, opposite the imaging components, or it may be formed as a flexible layer on the entire shell of the pill (either along the outer side of the shell, or along the inner side), or it may be formed on part of the shell of the pill. Furthermore, whether the energy harvester is within the capsule or along the capsule shell, it may be fabricated monolithically on the same wafer as the power management unit, or separately connected.

According to the invention, the antenna can be formed either inside the pill body or along the shell of the pill either inside or outside of the capsule. If formed on the shell of the pill (either inside surface or outside), it can also be formed on top of or underneath an energy harvesting unit layer.

BRIEF DESCRIPTION OF THE DRAWINGS

The invention may be better understood by reading the following detailed description with reference to the accompanying figures, in which:

FIG. 2A is showing the black-body equation.

FIG. 6I is a schematic showing an alternate embodiment where the inner surface of the energy harvesting section of the capsule itself is made of a lens.

DETAILED DESCRIPTION OF THE PREFERRED EMBODIMENTS

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention.

As mentioned, earlier, one disadvantage limiting capsule capability is battery life. Based on size of the capsule, batteries that could be used in the capsule have only enough energy to support about 8 hours with very less functionality. This 8 hrs. time is adequate to pass through the small intestine but not the large intestine. If battery life can be extended beyond their normal 6-8 hours capsule operation up to 72 hours, the large intestine can also be evaluated. Even longer battery life would allow imaging throughout the system at normal speed as well as slowed speed. Without external control 2 frames per second are captured. Methods of motion control, will result in more pictures taken and a slower passage through the small intestine consuming more battery life. Constrained by size that can be conveniently swallowed, batteries currently used fit in the 11 mm by 26 mm capsule size. A typical battery used is a silver oxide battery similar to battery number 394 from Energizer. This battery has 60 ma-h capabilities with a circumference of 9.5 mm and a thickness of two cells of 7.2 mm. Higher capacity batteries would have either larger circumference or would be thicker.

According to this invention, an approach to extend the battery life is to replace batteries with rechargeable batteries and/or replace by energy harvester. In standard capsule, an energy source for recharging the battery as the capsule migrates through the body is then necessary and it would be more painful to patient. According to this invention, the battery will be replaced by energy harvester, which helps to make the capsule more smaller, easier to swallow and could have more functionalities. The using of this energy harvester could also allow elimination of the batteries if the capsule requirements will match harvested power. Capsule size reduction would result with 8 mm of battery removed.

Figure 1:
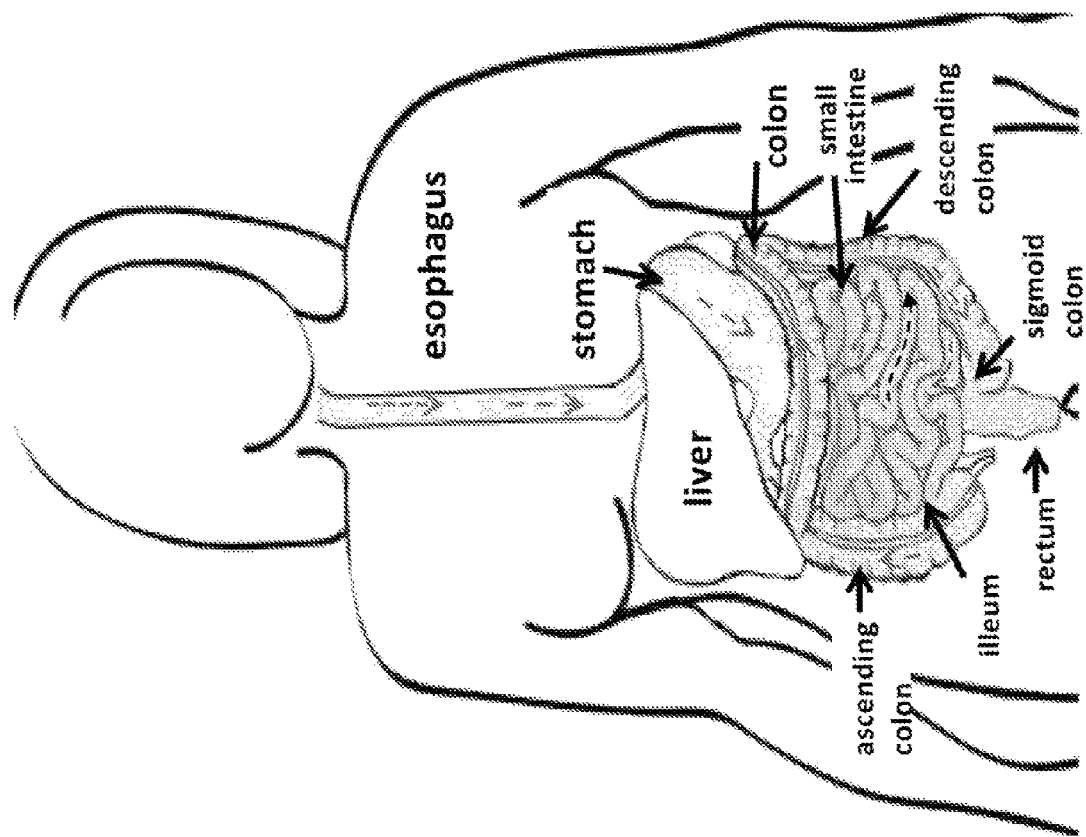
FIG. 1 is a schematic showing the cross-section view of human GI system. Internal arrow is showing how our foods are passing from mouth to rectum.
Figure 2B:
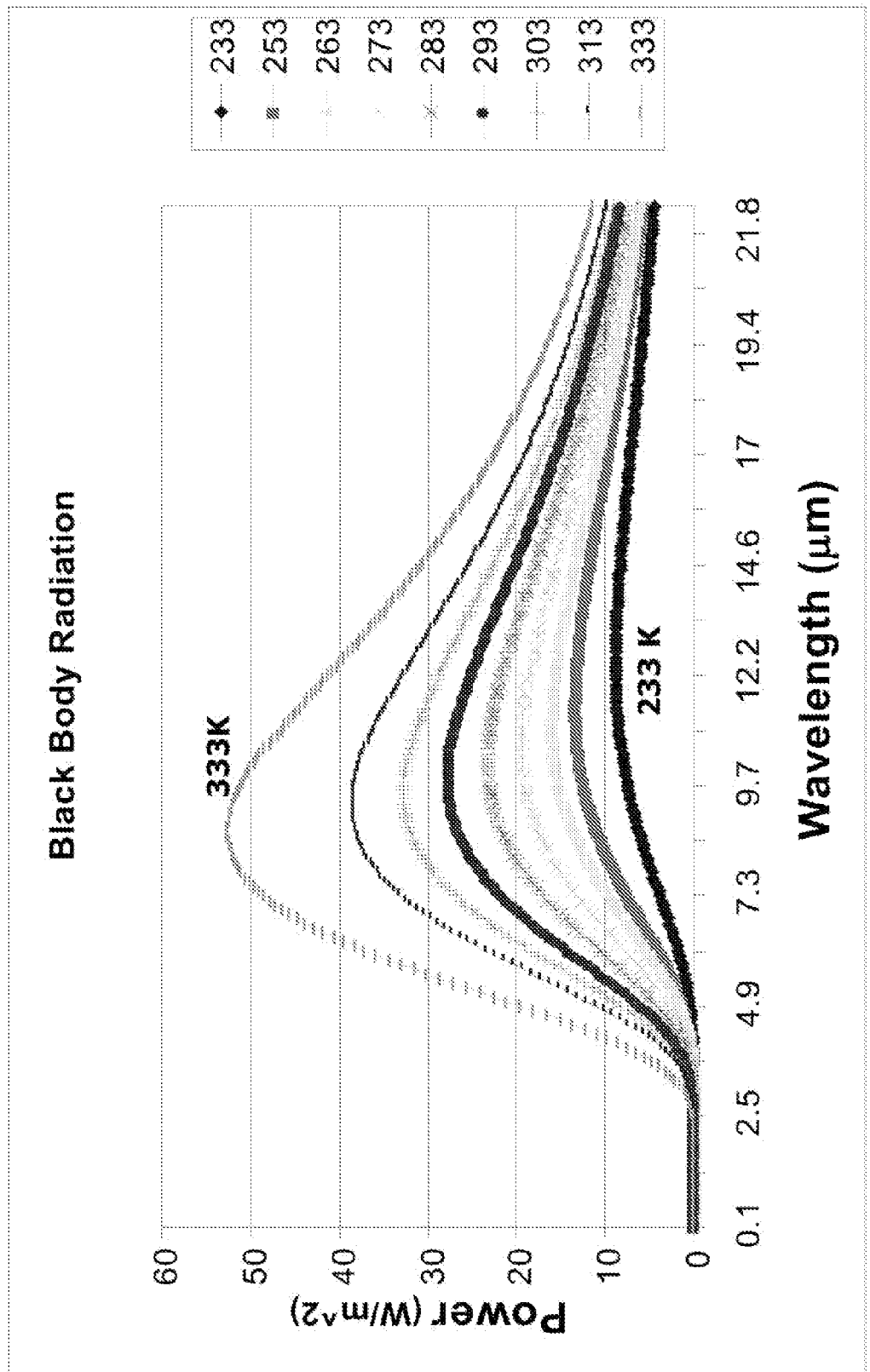
FIG. 2B is simulated results of energy available from blackbody radiation, with temperature (Kelvin) as the parameters.
Figure 2C:
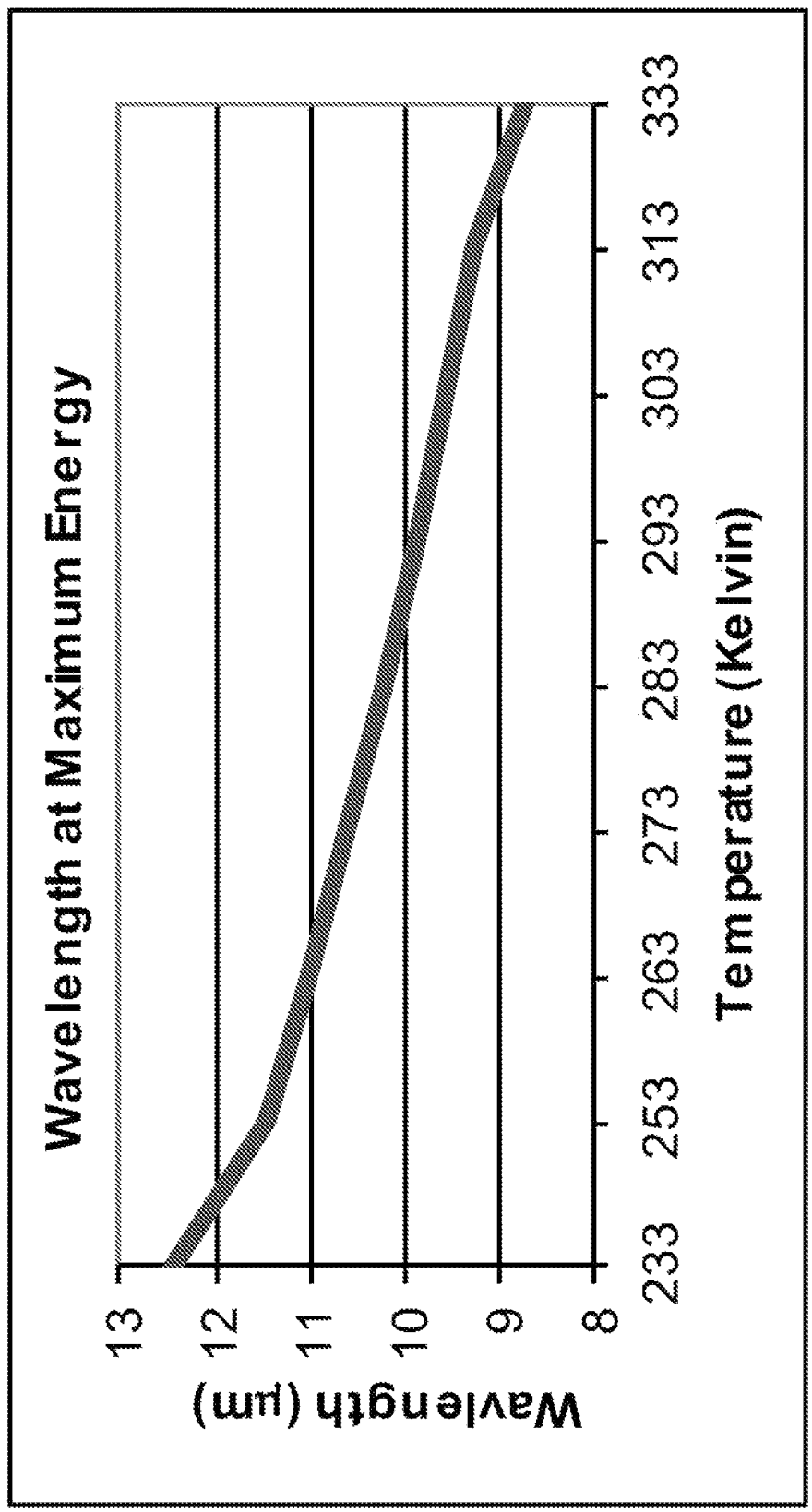
FIG. 2C is a graph showing the simulated results of the wavelengths of blackbody radiation at maximum energy.
Figure 3:
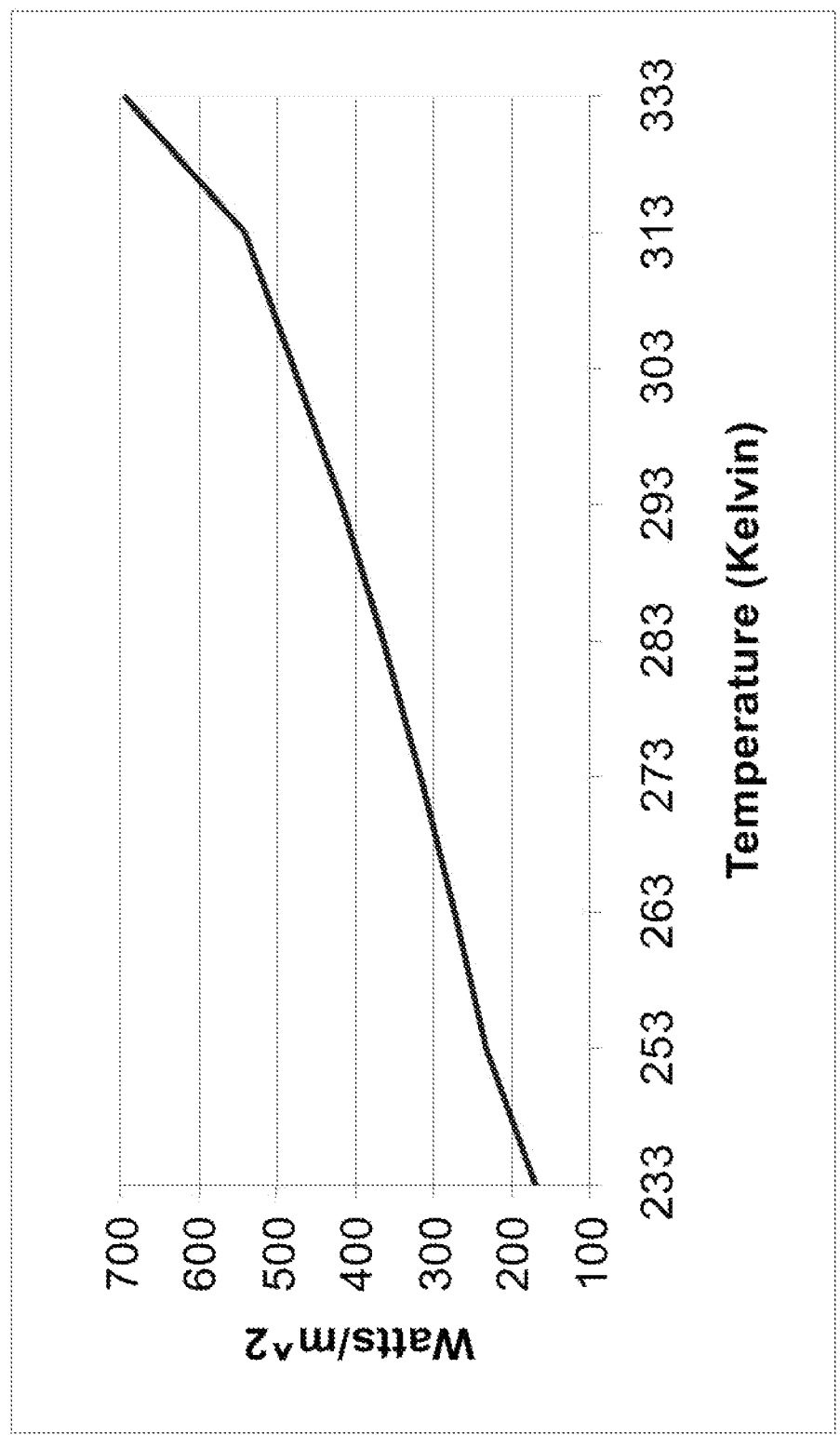
FIG. 3 is simulated results showing the available energy per square meter at various black-body temperatures.

Although several sources of energy within the human body are available, the preferred embodiment of this invention utilizes the energy harvesting from blackbody radiation. The human body radiates energy the same as any blackbody. This radiation energy is in the infrared wavelength. Radiation from a blackbody at a specific temperature is determined by Planck's blackbody radiation law, as illustrated in FIG. 2A and its simulated results at various temperature are shown in FIG. 2B. In this equation as illustrated in FIG. 2A, c=speed of light, k=Boltzman's constant, h=Planck's constant, .lamda.=wavelength, and T=temperature in Kelvin. As the temperature increases, the wavelength at the peak energy decreases. FIG. 2C shows the simulated results of peak energy wavelengths with functions of the temperature. The total amount of energy generated at a specific temperature are shown in FIG. 3, which depicts that available harvesting energy at body temperature of 310 Kelvin is about 500 watts per square meter.

According to this invention, there are also several other potential sources of energy within the body. One example is body vibration created due to the daily activities, other surrounding issues, and/or other organ functioning (e.g. heart, vein, artery etc.), from which energy could be harvested and feed to the system According to this invention, mechanisms for harvesting such energy might be electromagnetic (0.05 Watts per square meter), piezoelectric (6 Watts per square meter), or electrostatic (0.04 Watts per square meter). Another example is body heat, using a mechanism for thermoelectric harvesting. Alternatively, energy can be harvested from RF signals from outside the body. The signal from the imaging capsule is sent to an external receiver, typically held close to the body. RF signals from this receiver can help power the capsule. Although blackbody radiation is discussed in the most detail below, according to this invention, any of the above sources of energy can also be utilized, especially in combination.

Power consumption for current capsules is 25 mwatt. At 25 mWatt, the 60 ma-h (60 ma-h.times.3 v=180 mWatt) battery will be consumed in 7.2 hours. This can be extended indefinitely with the ability to harvest greater than 25 mwatt of continuous blackbody radiation. According to this invention there is 500 Watts per meter available to be harvested with in the human body. The preferred capsule diameter is 11 mm so the harvesting device should fit within this diameter. The peak wavelength for maximum energy for human body temperature, 310 Kelvin, is 9 microns. This maximum energy peak wavelength can be derived by determining the maximum energy wavelength of Planck's radiation law equation as shown in FIG. 2A. From the calculated results, as shown in FIG. 3, it gives the entire amount of blackbody energy generated and available for harvesting at a specific temperature. At 310K, approximately 500 W/m.sup.2 can be harvested.

Figure 4:
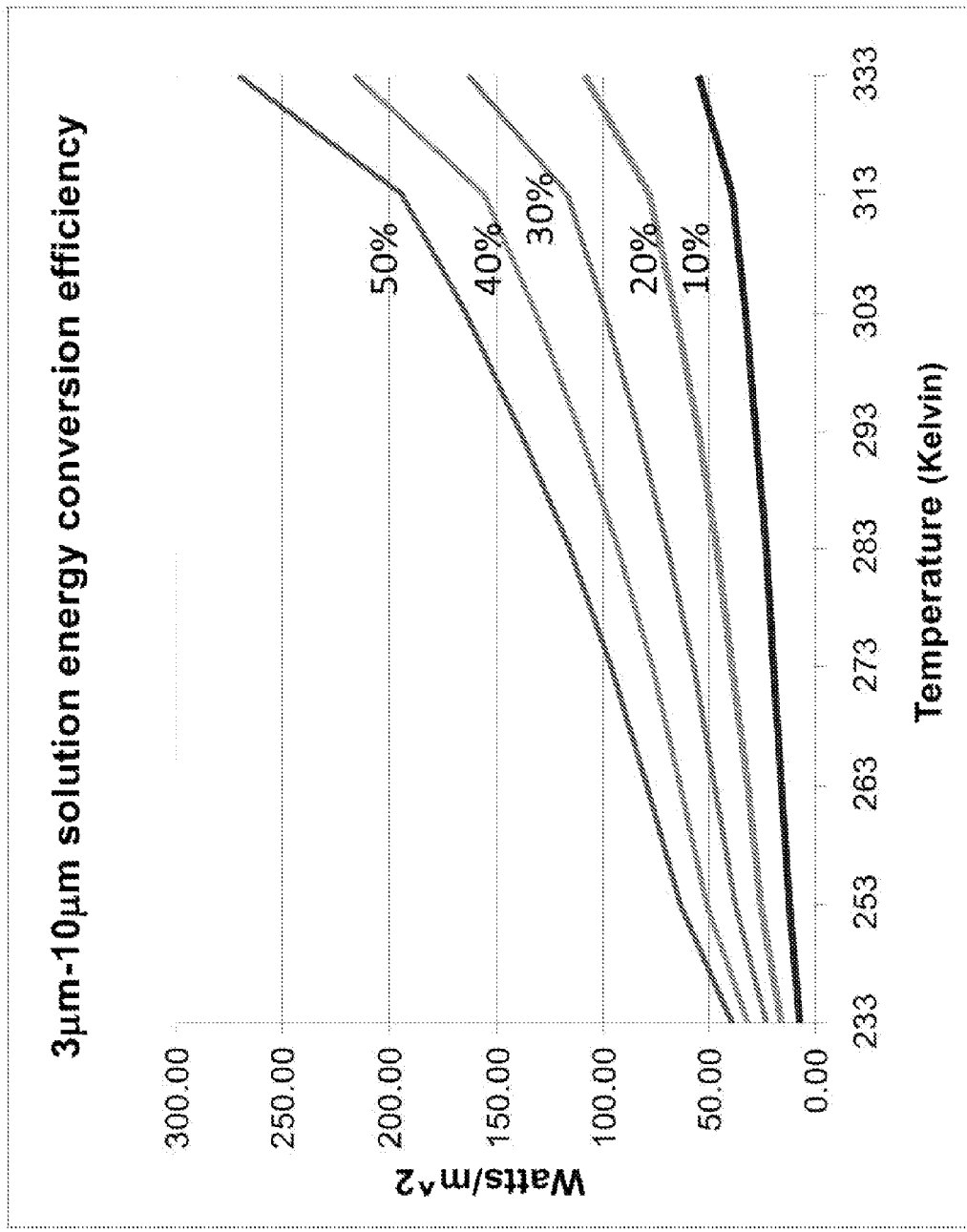
FIG. 4 is a graph showing simulated results of energy conversion efficiency with variation of the temperature.

This energy harvester which could be integrated into the capsule, is formed using the semiconductor material. Adjusting a material that would harvest at a peak frequency of 9 microns results in high intrinsic carriers and thus high dark current. Devices adjusted to high infrared wavelengths are normally operated at low temperatures (77 k). A compromise and workable solution is to adjust to the near infrared range that has less intrinsic carriers and lower dark current at 300 K. A potential tuning range is between 3 microns and 5 microns. Within this range the harvested energy for different harvest conversion efficiencies is shown in FIG. 4. If 50% efficiency harvesting is achieved, 47 watts per square meter is harvested. According to this invention, this harvest capability translates to 0.047 mwatt per square millimeter. The area of a harvest device that fits into a 7 mm diameter capsule (remember that the final goal is reduced size) would be 6.9 mm.times.6.9 mm=47.61 square millimeters resulting in 2.23 mWatt harvested. This would supply power to continuously charge the battery and have continuous capsule operation through put the digestive tract once the power of capsule electronic components is reduced. Focal plane array, read out integrated circuit and communication devices can be redesigned to consume less than 0.5 mwatt each by lower voltage and weak inversion operation resulting in a total of 1 mWatt. LED power consumption will be the main power used in short bursts. The LED's will be pulsed and need high energy (60 mW per LED times four LED's equals 240 mWatt) for short duration. Short durations are only for less than 1 msec three times every second if recording visible, infrared illuminated and dark every second. If only illuminating 1 msec three times per second then average power would only be 0.240 mw.times.3 or 0.72 mWatts and be well within the capability of harvesting. Total estimated operating average operating power would be 0.5 mWatt.times.2+0.72 mWatt=1.72 mWatt. As long as LED's are used for visible and infrared illumination a storage medium would be necessary to supply the temporary peak power surge. If a capacitor was made with thin CMOS gate oxide in the 47 square millimeter area there would be 15 microfarads of capacitance. Using I dt=C dv it can be shown that with 15 microfarads of capacitance would cause the voltage to be depleted. I dt=240 mWatts/3 v.times.1 msec=80 .mu.A-sec=15. mu.f.times.dv. dv=5.33 volts. Batteries will need to be used until a solution of capacitance more than an order of magnitude greater is available.

Figure 5:
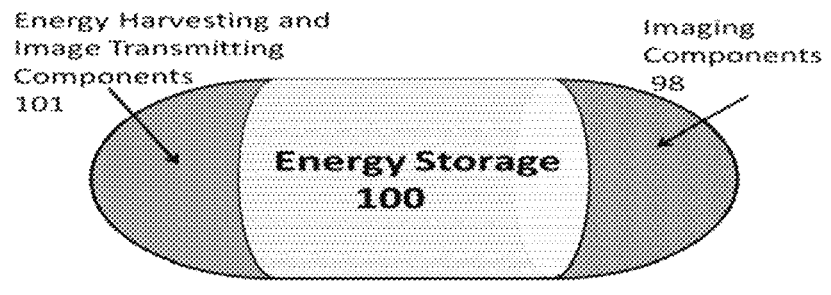
FIG. 5 is a schematic showing the main parts of the endoscope capsule in the preferred embodiment, according to this invention.

FIG. 5 shows the generalized preferred embodiment of endoscopy capsule system, according to this invention. On one end of the capsule is the imaging section 98, in the middle is the energy storage/management section 100, and on the opposite side is the energy harvester and communication components 101.

Figure 6A:
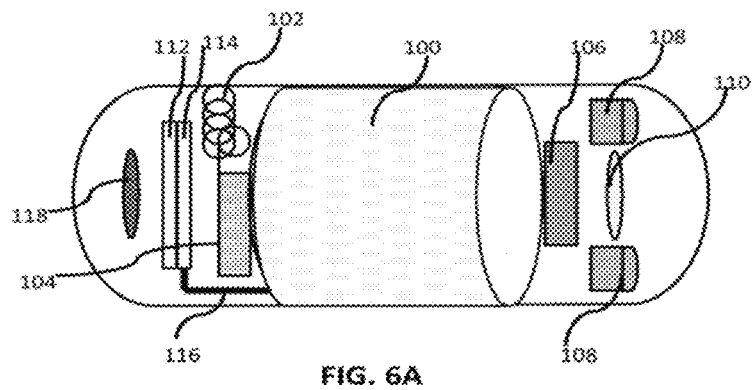
FIG. 6A is a schematic showing the preferred embodiment of this invention for endoscope system, integrating with an energy harvester.

FIG. 6A shows the preferred embodiment of this invention for endoscope system, integrating with an energy harvester. The middle section 100 is the power storage section connected to management system (not shown here in details) which includes electronics comprising with inverter, storage, and energy harvester, explained later. As a storage, capacitor or rechargeable battery or their combination is integrated and placed in middle section 100. In one end of the capsule all the signal processing electronics and part or whole of the antenna are housed. Main components this consists of an antenna 102, a transmitter 104, and others (not shown here). The imaging section 98 comprises a focal plane array (a.k.a. image sensor) 106 with a CMOS readout integrated circuit built in, emitter source (e.g. LEI) 108 provide illumination for imaging purposes, while a lens 110 focuses light in the desired spectrum on the focal array. Power for the focal array 106 and light emitter 108 is provided by the energy storage section 100. The energy storage section 100 is placed in the body of the capsule next to the imaging section, and takes up most of the space within the capsule. Making smaller will not only makes the capsule more compact, but also reduces the power consumption which enables it to capture more images and include more functionality. According to this invention, energy harvester, could be with or without battery. If battery is used, the only one battery may need. The energy harvester 112 and power management unit 114 are placed for optimal energy absorption and connected to each other. Alternatively, the power management unit 114 can be integrated into the energy harvester 112 itself, as discussed in more detail below. A lens 118 focuses infrared light on the energy harvester 112, and can be formed from any material which is suitable for this purpose. For example, magnesium fluoride, calcium fluoride, zinc selenide, barium fluoride, AMTIR I, arsenic fluoride, zinc sulfide, sapphire, silicon, germanium, or some combination thereof.

Figure 6B:
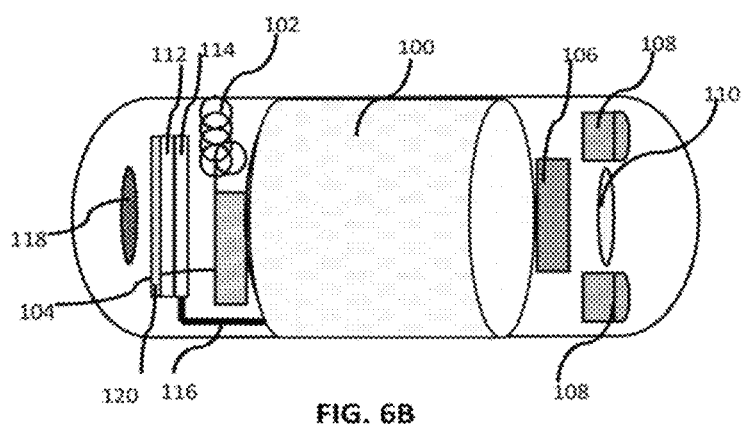
FIG. 6B is a schematic showing an alternate embodiment where the second energy harvester harvest energy through vibration and is connected to the first energy harvester.
Figure 6C:
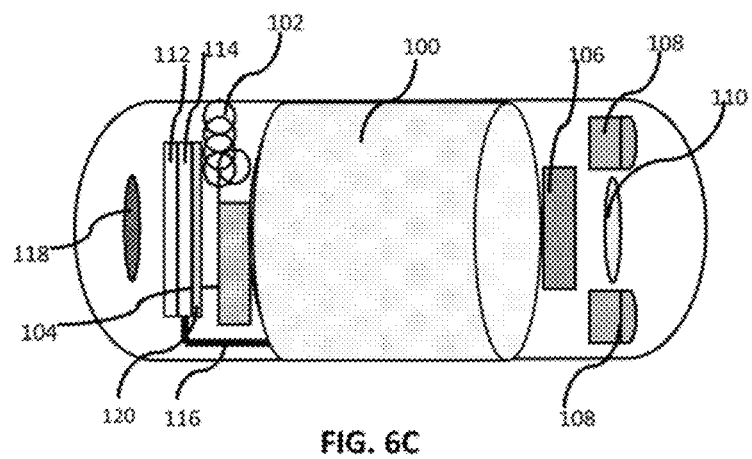
FIG. 6C is a schematic showing an alternate embodiment where the second energy harvester harvest energy through vibration and is connected to the power management unit.
Figure 6D:
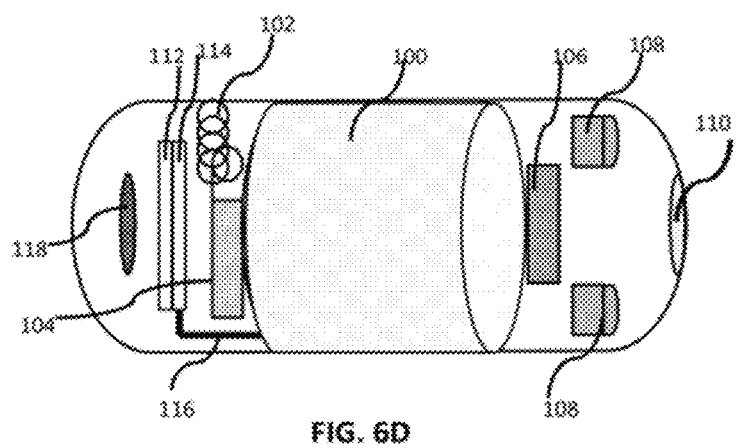
FIG. 6D is a schematic showing an alternate embodiment where the first lens is placed on the inner surface of the shell.
Figure 6E:
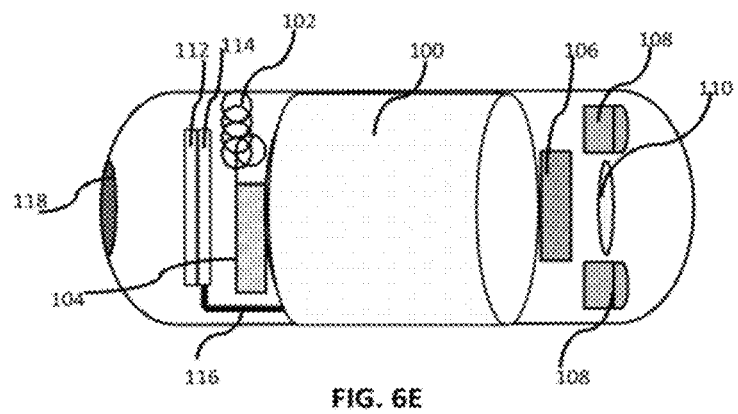
FIG. 6E is a schematic showing an alternate embodiment where the second lens (118) is placed on the inner surface of said shell.
Figure 6F:
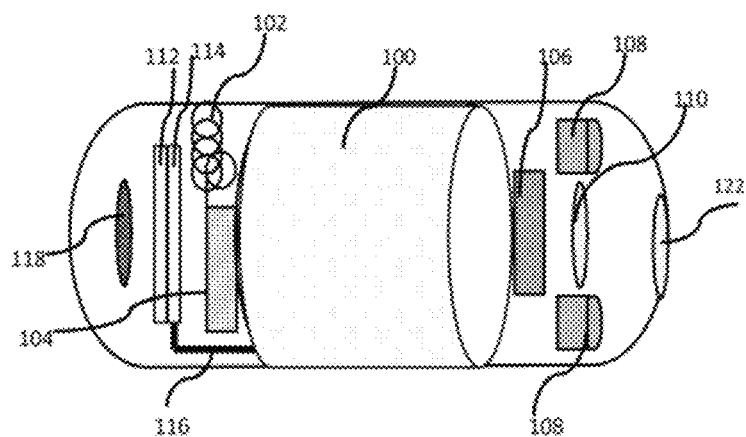
FIG. 6F is a schematic showing an alternate embodiment where an additional lens on the imaging section of the lens and is placed on the inner surface of said shell.
Figure 6G:
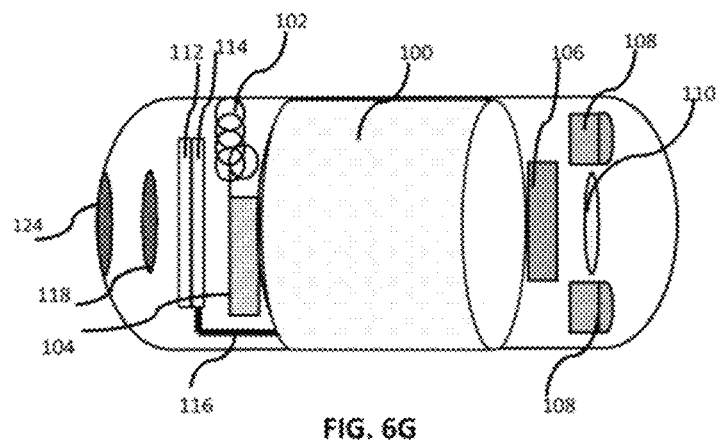
FIG. 6G is a schematic showing an alternate embodiment where additional lens on the energy harvesting section of the capsule and is placed on the inner surface of said capsule.
Figure 6H:
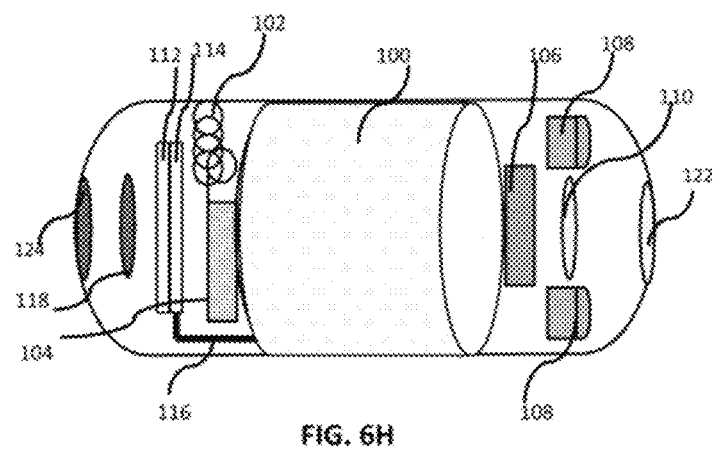
FIG. 6H is a schematic showing alternate embodiment where two new lenses, one added to the imaging section of the capsule, and a new lens added to the energy harvesting section of the capsule, where both these lenses, are on the inner surface of the capsule shell.
Figure 6I:
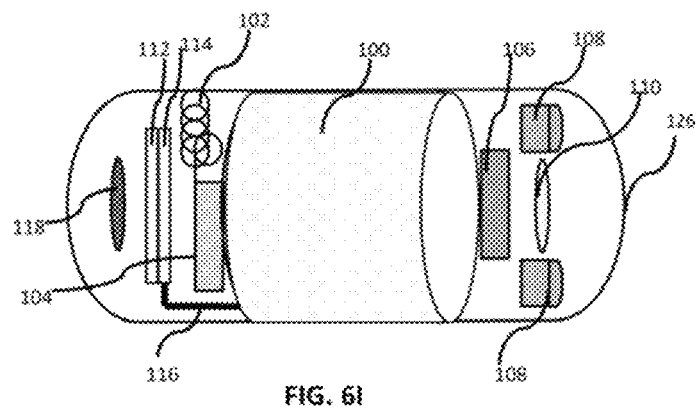
FIG. 6I is a schematic showing an alternate embodiment where the inner surface of the imaging section of the capsule itself is made of a lens.
Figure 6J:
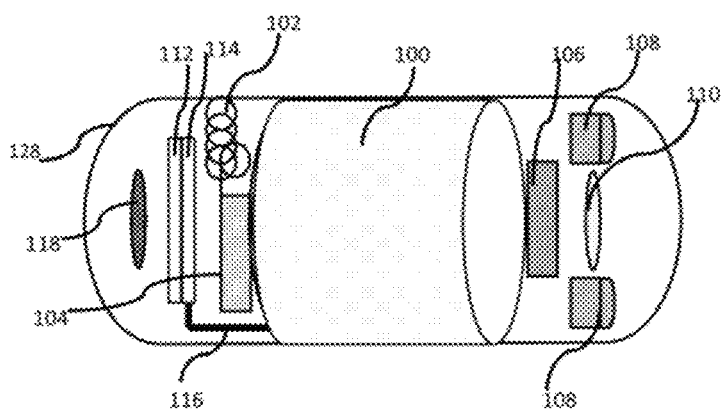
FIG. 6K is a schematic showing an alternate embodiment where the inner surface of the capsule on both sides is made of lenses.
FIG. 6L is a schematic showing an alternate embodiment where the lens is placed on the inner surface of the capsule shell and the image sensor array is placed behind said lens.
Figure 6K:
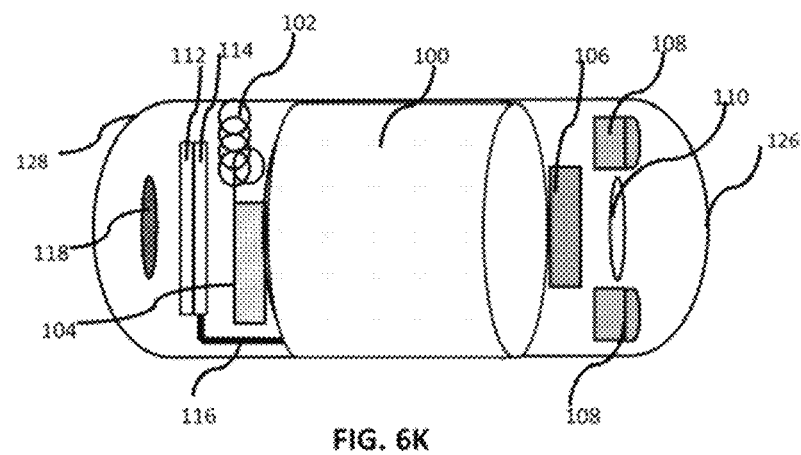
Figure 6L:
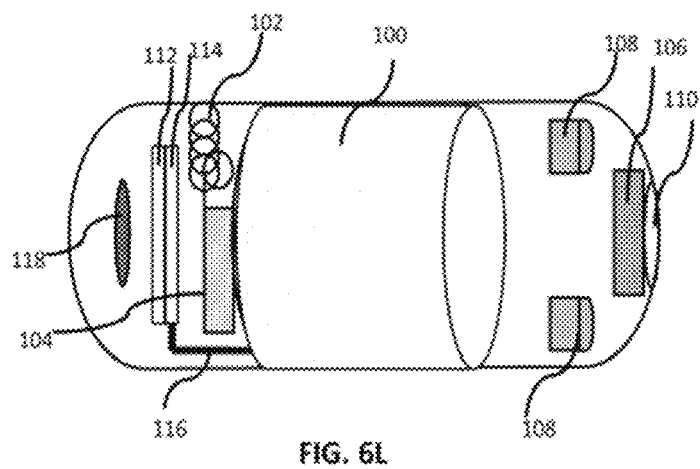
Figure 7:
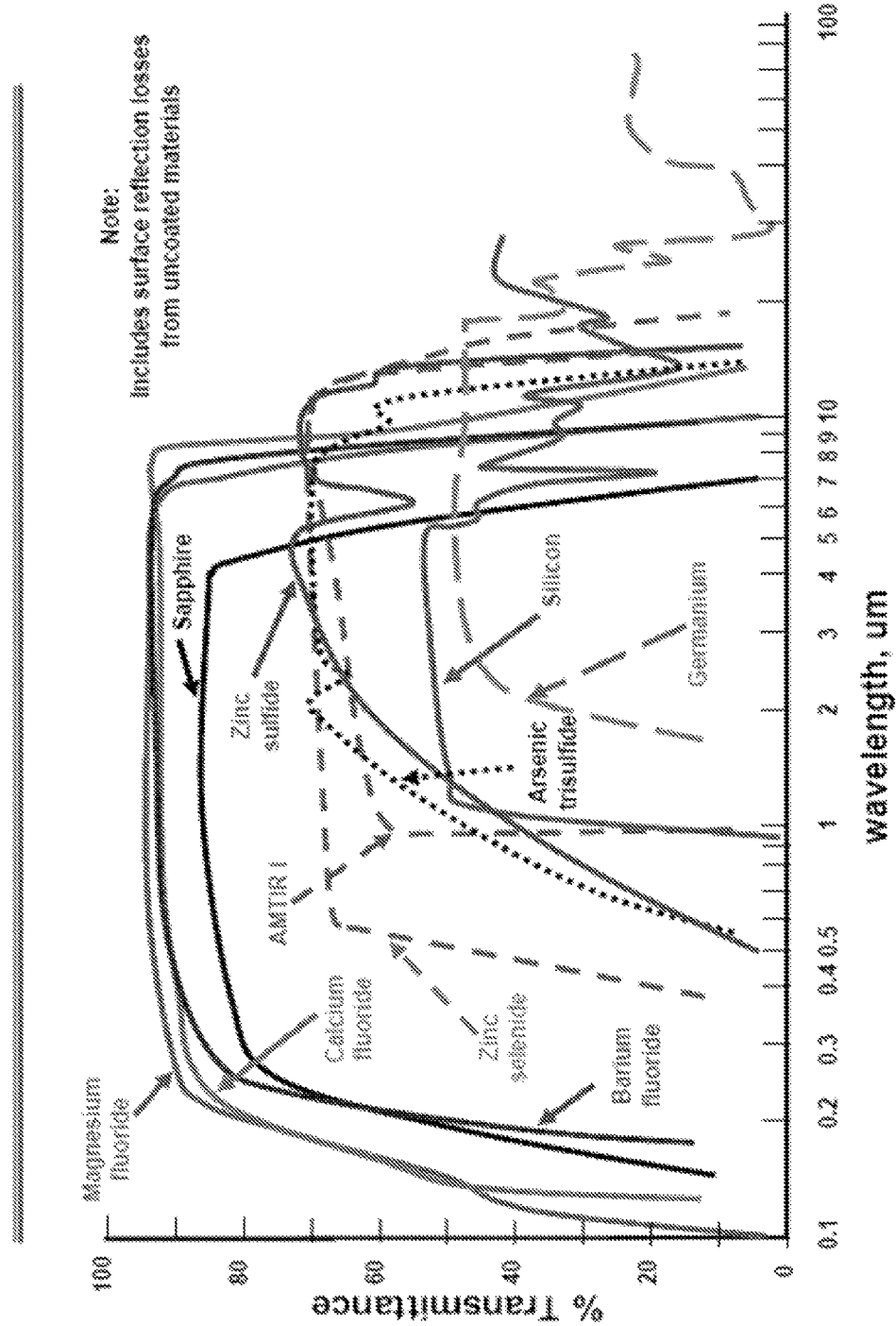
FIG. 7 is a graph showing the suitability of various materials as lenses which transmit broad radiation wavelengths.

FIG. 6B and FIG. 6C are schematics showing alternate embodiments according to this invention, wherein the same parts in FIG. 6B and FIG. 6C represent the similar parts in FIG. 6A, so that repeated explanation is omitted here. The only difference between FIG. 6A with FIG. 6B and FIG. 6C, is that an additional energy harvester (second energy harvester) 120 is located within the capsule in FIG. 6B and FIG. 6C. The second energy harvester 120 in FIG. 6B harvest energy through movement/vibration. In FIG. 6B the second energy harvester 120 is connected to the first energy harvester 112. Alternatively in FIG. 6C the second energy harvester 120 is connected to the power management unit 114. FIG. 6D and FIG. 6E are schematics showing alternate embodiments according to this invention, wherein the same parts in FIG. 6D and FIG. 6E represent the similar parts in FIG. 6A, so that repeated explanation is omitted here. The only difference between FIG. 6A with FIG. 6D and FIG. 6E, is the location of one of the lenses, either the first lens (110) or the second lens (118). In FIG. 6D the first lens is placed on the inner surface of the shell and in FIG. 6E, the second lens (118) is placed on the inner surface of said shell. For these embodiments to be possible, the lens would have to be of flexible material. FIG. 6F, FIG. 6G and FIG. 6H are schematics showing alternate embodiments according to this invention, wherein the same parts in FIG. 6F, FIG. 6G and FIG. 6H represent the similar parts in FIG. 6A, so that repeated explanation is omitted here. The only difference between FIG. 6A with FIG. 6F, FIG. 6G and FIG. 6H, is that new lenses are added to each of these embodiments (FIG. 6F, FIG. 6G and FIG. 6H) and placed on the inner surface of the shell. In FIG. 6F, a new lens 122 has been added to the imaging section of the lens and is placed on the inner surface of said shell. In FIG. 6G, a new lens 124 has been added to the energy harvesting section of the capsule and is placed on the inner surface of said capsule. In FIG. 6H a new lens 122 has been added to the imaging section of the capsule, and a new lens 124 has been added to the energy harvesting section of the capsule. Both these lenses, 122 and 124 are placed on the inner surface of the capsule shell. FIG. 6I, FIG. 6J and FIG. 6K are schematics showing alternate embodiments according to this invention, wherein the same parts in FIG. 6I. FIG. 6J and FIG. 6K represent the similar parts in FIG. 6A, so that repeated explanation is omitted here. The only difference between FIG. 6A with FIG. 6I, FIG. 6J and FIG. 6K, is that the in these embodiments, the capsule shell itself is made of lenses. In FIG. 6I, the inner surface of the capsule itself (the imaging section of the capsule) is made of a lens 126. In FIG. 6J, the inner surface of the capsule itself (the energy harvesting section of the capsule) is made of a lens 128. In FIG. 6K the inner surface of the capsule on both sides is made of lenses, the inner surface of the capsule in the imaging section is made of a lens 126 and the inner surface of the capsule in the energy harvesting section is made of a lens 128. FIG. 6L, is the schematic showing alternate embodiment according to this invention, wherein the same parts in FIG. 6L, represents the similar parts in FIG. 6A, so that repeated explanation is omitted here. The only difference between FIG. 6A with FIG. 6L, is that in this embodiment, the location of the lens or the image sensor array or both the lens and image sensor array is different. In FIG. 6L, the lens 110 is placed on the inner surface of the capsule shell and the image sensor array 106 is placed behind said lens. For FIG. 6L, to be possible, both the lens and image sensor array would have to be made of flexible material As long as the connections described above are maintained, the placement of the various components can be placed in many different ways. For example, the focal array 106 or energy harvester 112 can be formed as layers which cover all or part of the outer shell of the capsule. Such a choice increases the surface area of both devices and improves performance of the device as a whole. Additionally, the antenna might be formed as a layer disposed below or on top of the focal array or harvester layer. If the antenna is formed on top, then it should be formed from a material which does not absorb wavelengths of interest, otherwise it might hinder performance of the device as a whole. Any combination of the above descriptions is possible. FIG. 7 shows a graph of various possible materials and their suitability for transmitting IR wavelengths. The transmitter 104 and antenna 102 are also located in the capsule section 101. The power management unit 114 is connected to the energy storage section 100 through connection 116 to control flow of energy to and from the energy storage 100, and then all other components which require power (the transmitter 104, focal array 106, and light emitter 108) are connected to the power management unit 114.

Figure 8:
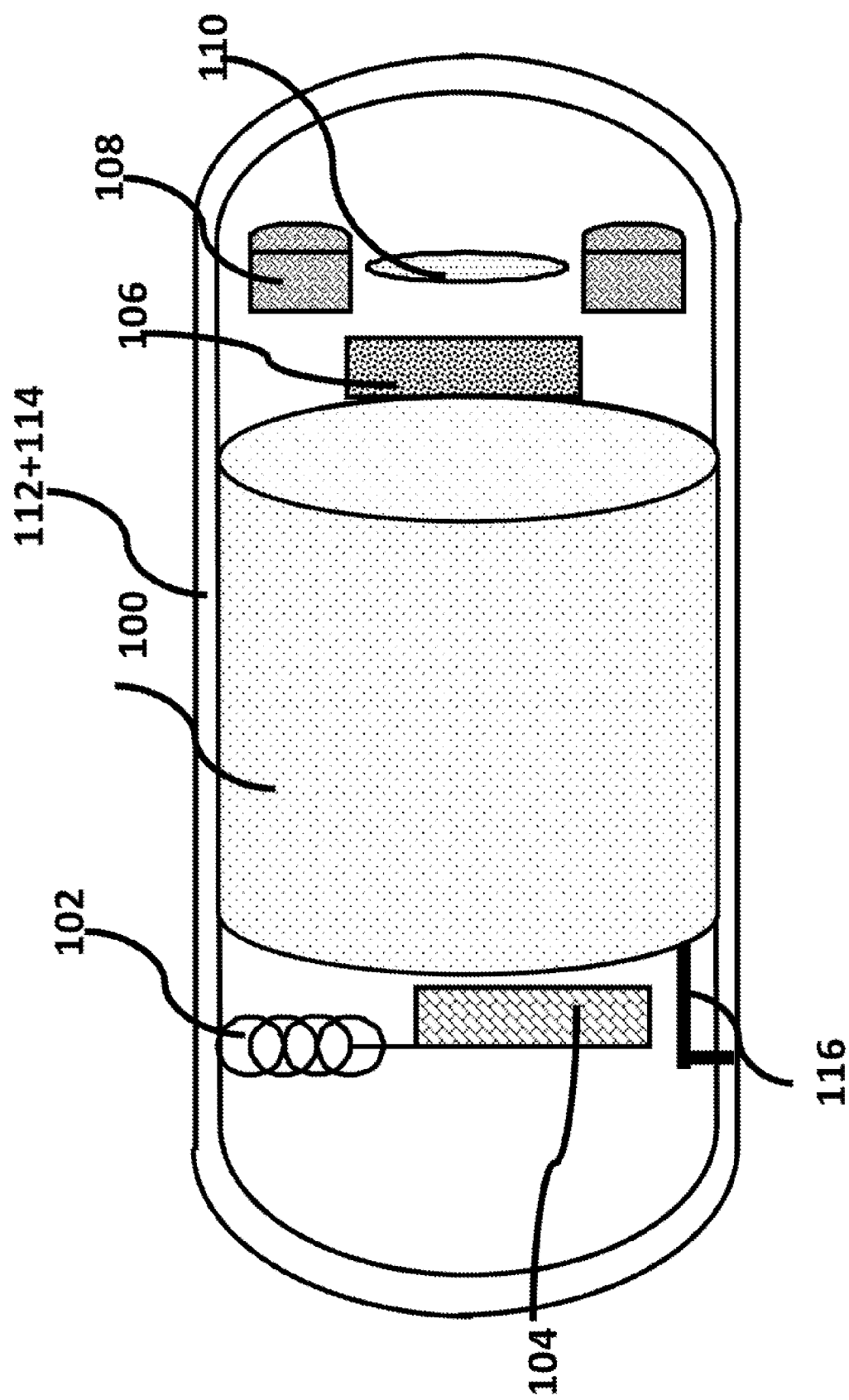
FIG. 8 is a schematic showing an another preferred embodiment of a endoscope capsule system according to this invention, wherein the energy harvesting component is shown as a layer which encases the entire device, covering the entire surface.
Figure 9A:
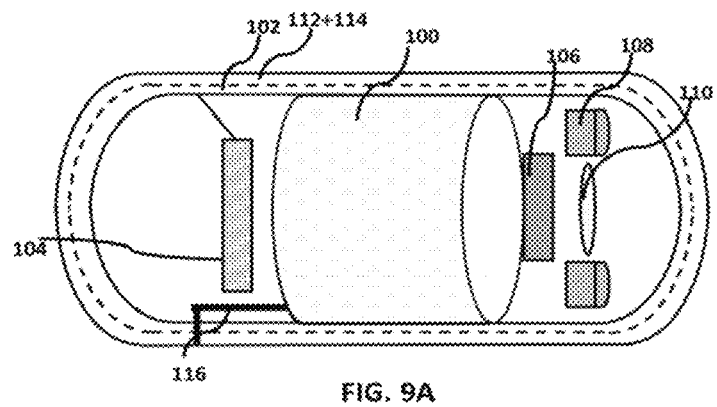
FIG. 9A is a schematic showing an alternate embodiment of the endoscope capsule system according to this invention, wherein the antenna as shown as a layer which encases the entire device, and the energy harvesting device and power management system then encases the antenna.
Figure 9B:
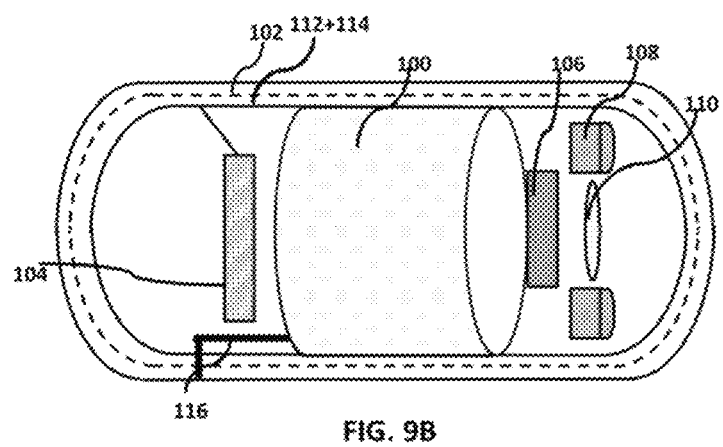
FIG. 9B is a schematic showing an alternate embodiment of the endoscope capsule system according to this invention, wherein the energy harvesting device and power management system as shown as a layer which encases the entire device, and the antenna then encases the energy harvesting device and power management system.
Figure 10A:
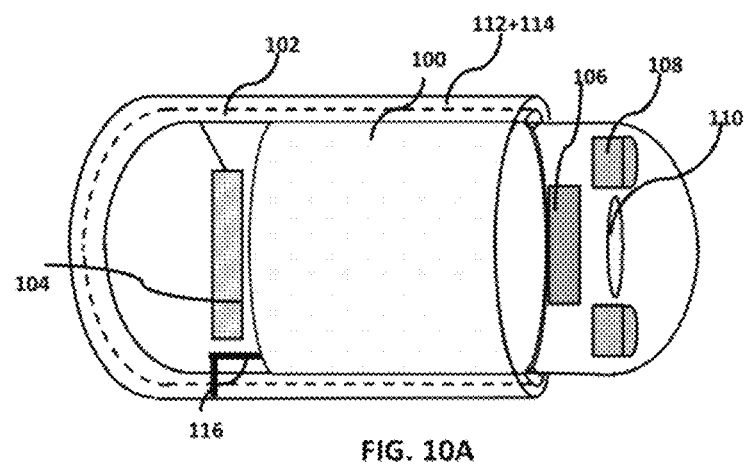
FIG. 10A is a schematic showing an alternate embodiment of the endoscope capsule system according to this invention, wherein the antenna as shown as a layer which partially encase the device, and the energy harvesting device and power management system then encases the antenna.
Figure 10B:
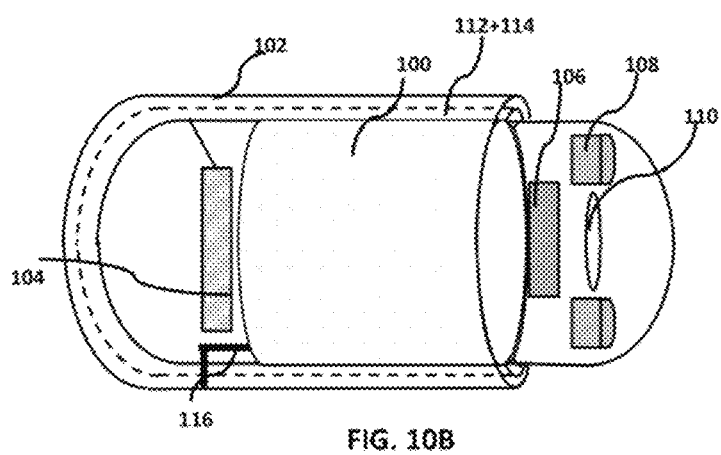
FIG. 10B is a schematic showing an alternate embodiment of the endoscope capsule system according to this invention, wherein the energy harvesting device and power management as shown as a layer which partially encase the device, and the antenna then encases the energy harvesting device and power management.

FIG. 8 is a schematic showing the alternate endoscope capsule in the preferred embodiment, according to this invention, wherein same numerals are used for the similar parts, so that repeated explanation is omitted here. In this preferred embodiment where the focal array 106 remains the same, but the energy harvester 112 and power management unit 114 are integrated and formed as a layer which covers the entire outer surface of the pill. FIG. 9A is another alternate embodiment, except where the antenna 102 is also formed as an outer layer, placed below the energy harvester 112 and power management system 114. FIG. 9B is another alternate embodiment, except where the energy harvester 112 and power management system 114 are also formed as an outer layer, placed below the antenna 102. FIG. 10A is another embodiment of this endoscopic capsule invention, where the antenna 102 layer is formed on the outer layer and encased by the energy harvester 112 and power management system 114 layer cover the entire surface except for the imaging section. FIG. 10B is another embodiment of this endoscopic capsule invention, where the energy harvester 112 and power management system 114 layer are formed on the outer layer and encased by the antenna 102 layer cover the entire surface except for the imaging section. This embodiment might be favorable in situations where the materials used for the antenna and/or energy harvester might block the wavelengths which the imager is designed to detect.

As an another example of the embodiments (not shown in here), the focal array 106 might be a layer which covers the battery section and imaging section, while the energy harvester 112 might be a layer which covers the remaining surface area without overlapping the focal array 106. The antenna might then be a layer which is located under or over one or both of the layers 112 and 106. As another example, the focal array 106 and energy harvester might be layers which cover the entire pill, stacked on top of one another. The antenna could then be placed inside, or formed as a layer under the layers 106 and 112, over the layers 106 and 112, or even placed between the layers 106 and 112.

Figure 11:
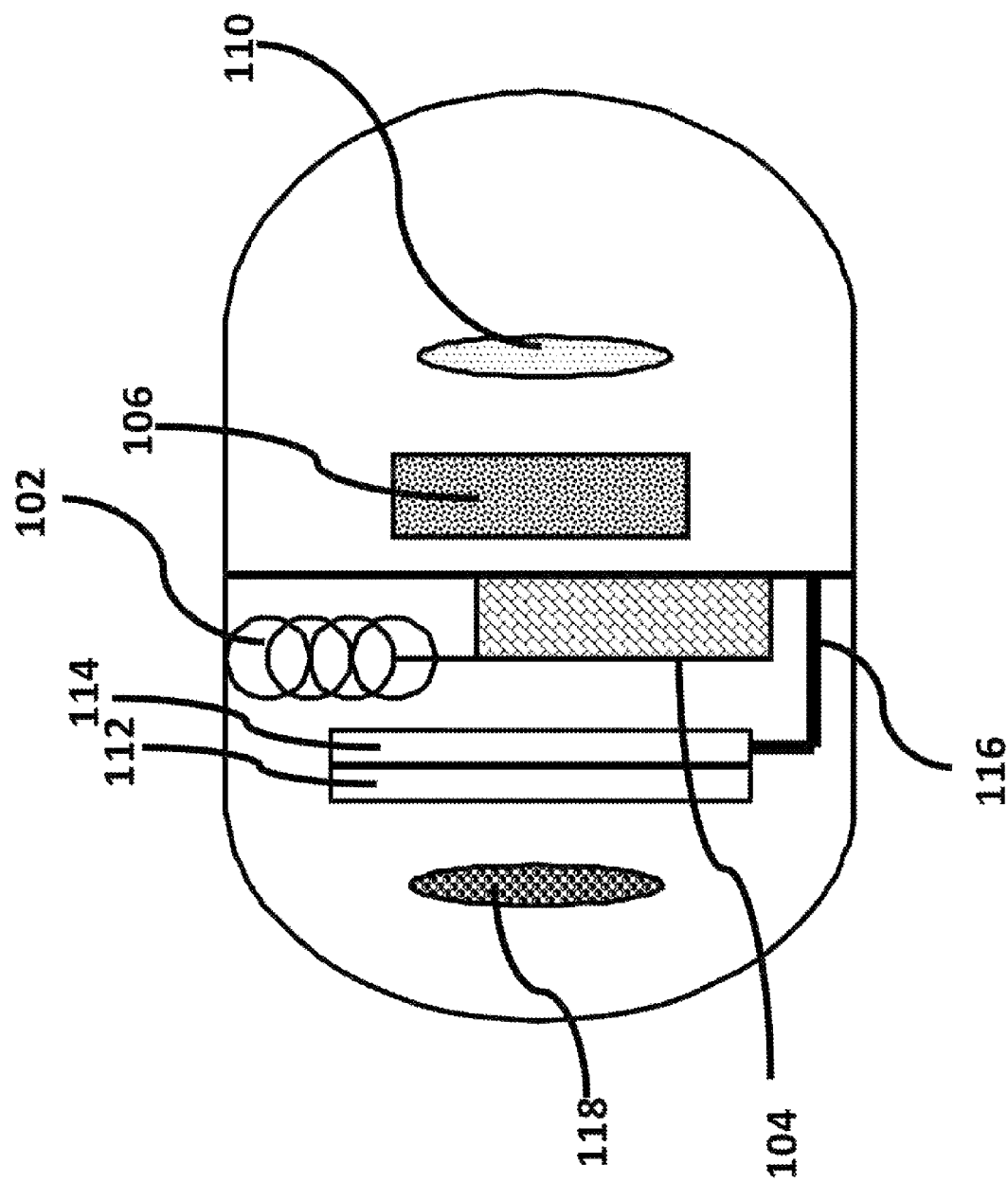
FIG. 11 is a schematic showing an alternate embodiment of endoscope capsule system according to this invention.

FIG. 11 is a schematic showing a another preferred embodiment of this current invention for endoscope capsule system, wherein the same numerals represent the similar parts as explained in FIGS. 8, and 8-10, so that repeated explanations are omitted here. According to this invention, the battery is completely omitted. In this case, the harvester generates energy and feed directly to the system. This is system can be with and without light emitters. As Light emitters consume more power, light emitter can be omitted. As explained earlier, harvesting power is enough to take the image, signal processing, and transmitting to outside. The light emitter 108 is only necessary when the focal array 106 is designed to sense visible light. If, instead, the focal array is designed to sense outside the visible spectrum only, such as infrared imaging, then the light emitter can be omitted and the device as a whole can function on the harvested energy alone. The embodiment in FIG. 11 shows the endoscope-capsule as much reduced in size, but alternatively, the empty space in the middle can be utilized in a number of ways, as discussed further below.

The preferred embodiment of this invention for endoscope capsule system includes several sections, and the of them is the energy harvester device and its integration with power management system which can reduce the size and make it longer to operate more than 10 hrs. or so capturing GI's image, as it passes. The harvester technique is explained below, as an example, but not limiting the invention. For simplicity, we would provide an example in related to harvester which is made using high wavelength absorption material such as HgCdTe based material systems. However, it can be related to other semiconductor materials such as InSb, etc.

Figure 12A:
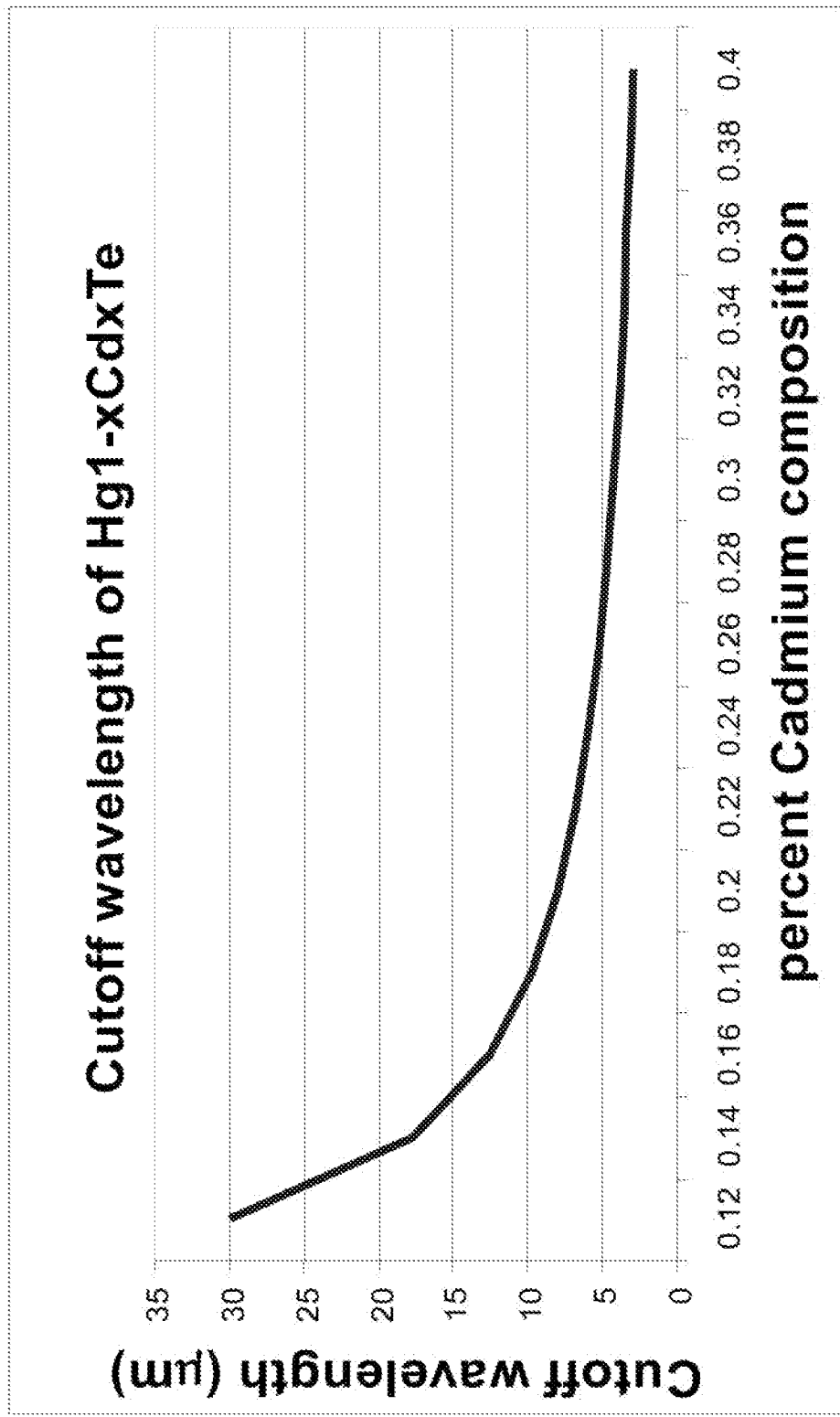
FIG. 12 is the graphs showing (A) cut-odd wavelengths, and (B) absorption coefficient for HgCdTe depending on the percentage of Cd.
FIG. 12C is a graph showing the quantum efficiency of HgCdTe device as an example, according to this invention.
Figure 12B:
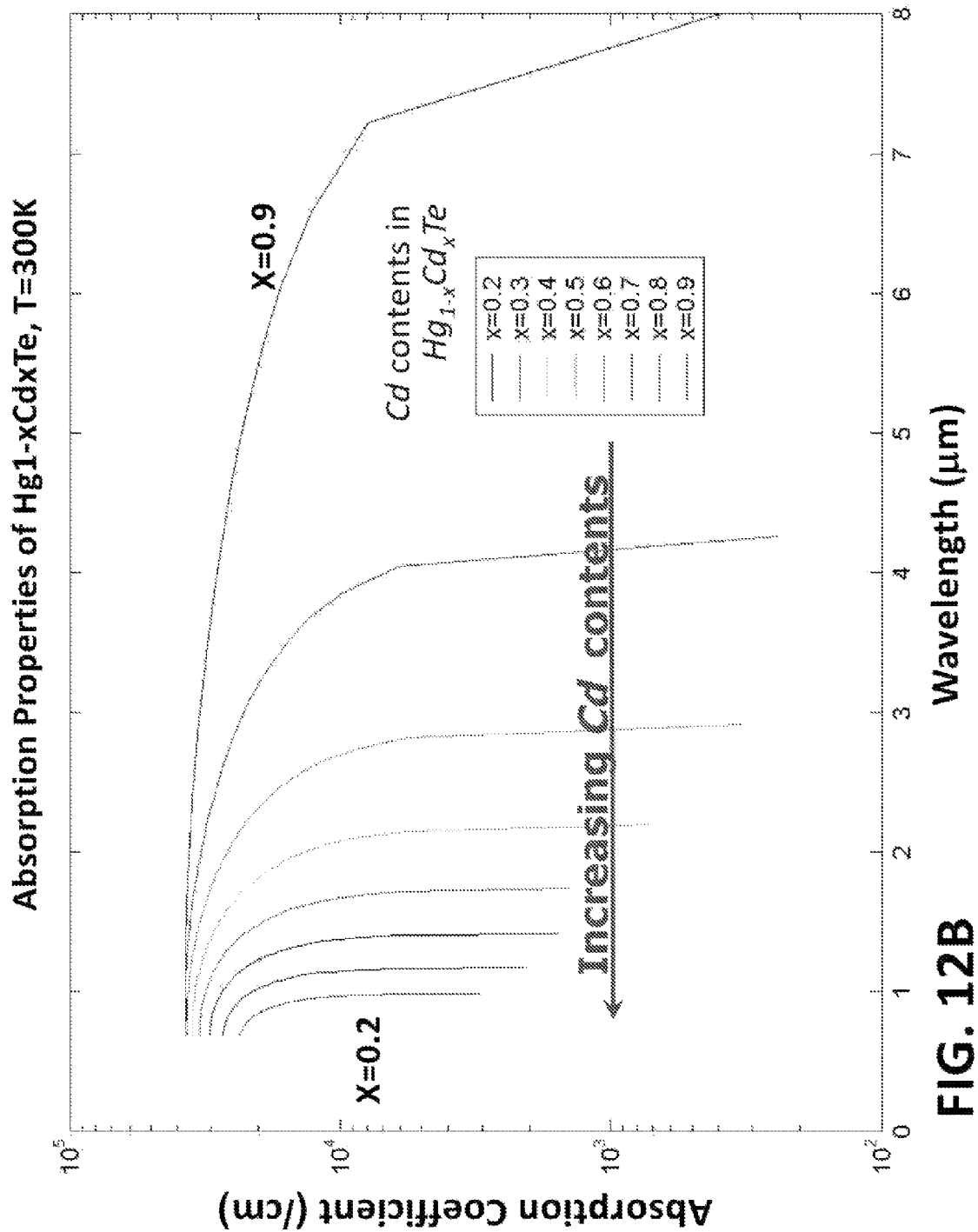
Figure 12C:
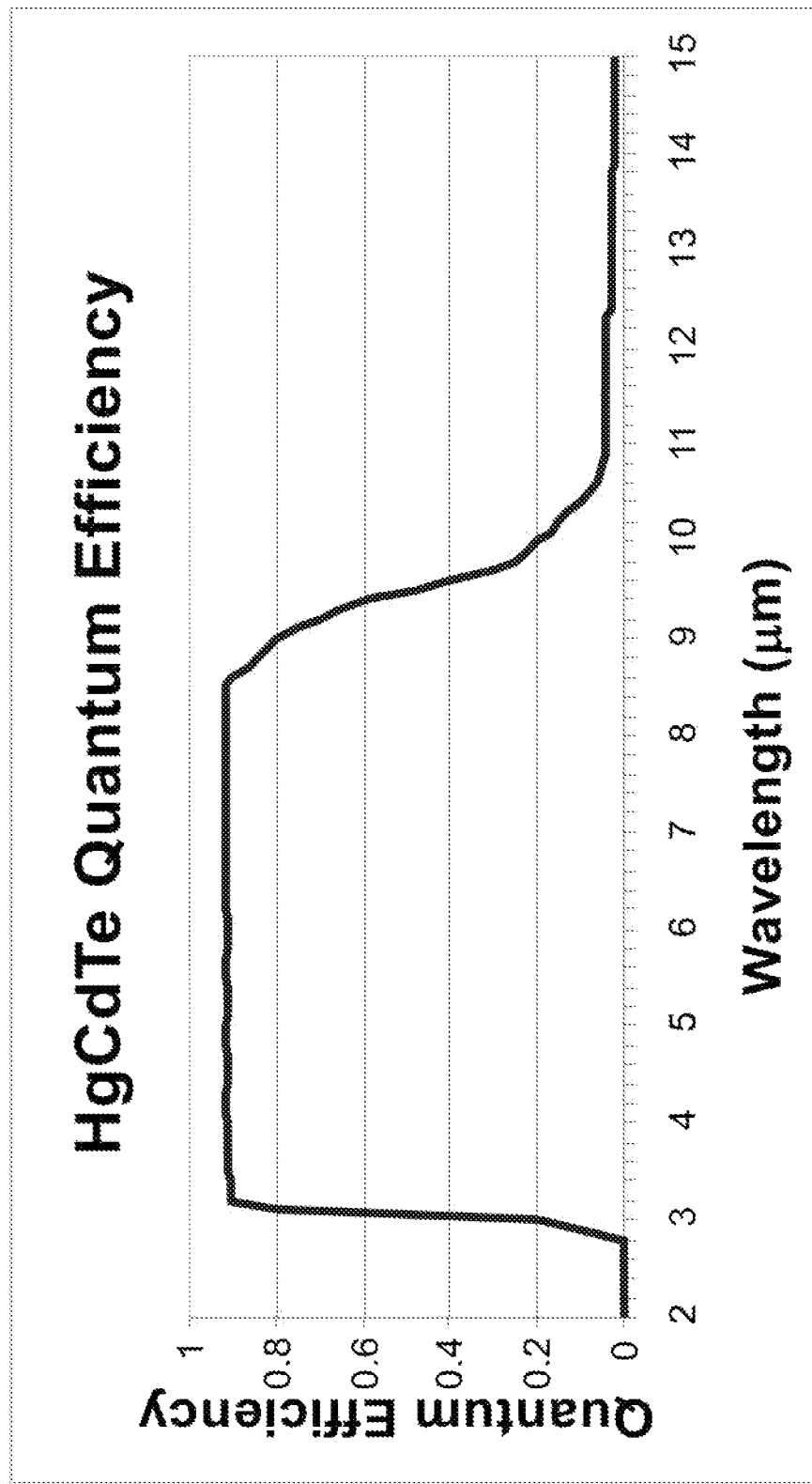

A preferred material for infrared harvesting is Mercury Cadmium Telluride (HgCdTe). HgCdTe's bandgap can be tuned between 0.8 .mu.m to 25 .mu.m. It has been determined that the bandgap can be adjusted by varying the percentage of Hg versus Cd. The equation showing this relationship is $Eg=-0.302+1.93x-0.81x^2+0.832x^3+(5.35 \times 10^{-4})T(1-2x)$ where x is the amount of cadmium (Cd). This equation is plotted in FIG. 12A. The absorption spectra of the HgCdTe with various Cd contents are calculated and it is show in FIG. 12B. Adjustment of cadmium versus mercury can result in a reasonable implementation that has the ability to harvest wavelengths from 3 .mu.m to 10 .mu.m. The upper limit of 10 .mu.m was chosen to maintain a reasonable forward voltage. There are several factors that contribute to infrared harvesting efficiency. The ability of a material of absorb energy in the wavelength of available energy is a key factor. This key factor determining the net conversion efficiency of harvester is quantum efficiency (QE). (QE) is the probability that an incident photon of energy Egwill deliver an electron to the external circuit. QE varies per wavelength for different solar harvesting technologies. FIG. 12C shows how QE varies in HgCdTe across wavelengths. Other factors affecting conversion efficiency are cell layer thicknesses, contact resistances and leakages To achieve the bandgap upper limit of 10 .mu.m, 17% Cadmium versus 83% mercury is used. Once energy is harvested, conditioning of that energy must be done to supply voltage and current to devices and charge batteries. Power management devices designed to interface between the infrared harvesting structure and output device can be designed with current CMOS technology. To have versatile output voltage range, a 0.35 .mu.m process with high voltage options up to 10 volts would be used. This will allow internal harvested voltages to go beyond 3 volts and be regulated to a desired 3 volt output.

According to this invention, if 30% efficiency of harvesting is achieved, 125 Watts per square meter is harvested. This harvest capability translates to 0.125 mWatt per square millimeter. The area of a circular harvest device that fits into the 11 mm diameter capsule would be 9.5 mm.times.9.5 mm.times.3.14=283 square millimeters resulting in 35.4 mwatt harvested. This would supply substantial power to continuously charge the storage element (e.g. capacitor or battery) and have continuous capsule operation throughout the digestive tract. Alternatively, if the harvest device is formed as a layer all along the capsule shell as well as a circular disk, harvested energy could be even higher. A harvester which is a layer covering only the battery section alone will have a surface area of approximately 275 square millimeters. Combined with the circular disk harvester, this would result in approximately 69.78 mwatt harvested.

Figure 13:
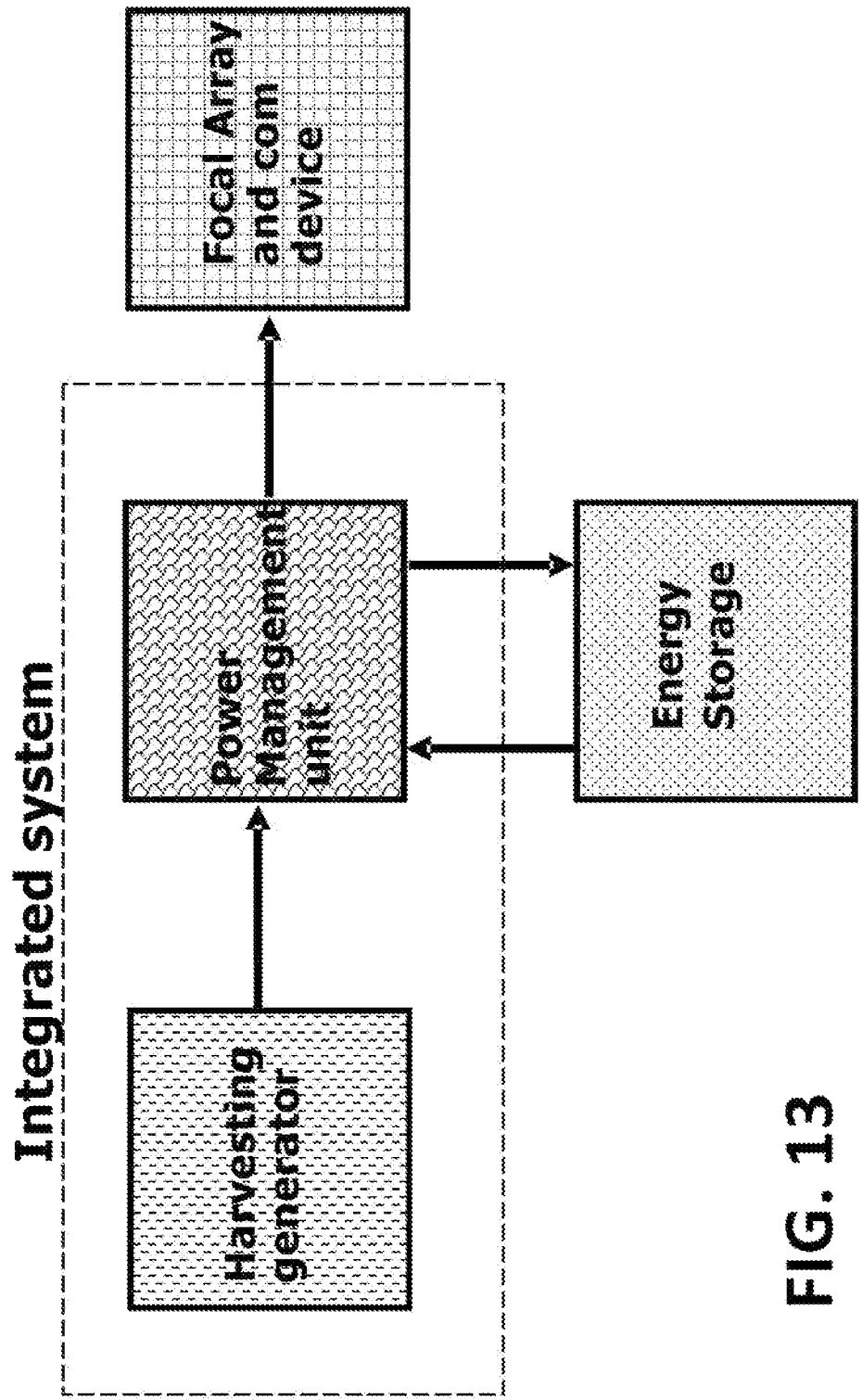
FIG. 13 is a schematic showing for the most basic description of how the components of the invention are to be connected according to this invention.

The specific structure of the preferred embodiments, as explained in FIGS. 5 to 12 is highly variable. Although the connections must be constant within every variation, the specific placement of each component can be changed in many ways, especially if the battery is been eliminated completely. FIG. 13 is a schematic showing the very basic method of connecting the components. An energy harvester and power management unit are integrated into a single unit, either monolithically formed on the same wafer, or fabricated separately and then stacked and connected with metal bumps. A energy storage (e.g. battery) is then connected to the power management unit, and the focal array and communication device are separately connected to the power management unit. The components must all be connected in roughly the same way. The power management unit and energy harvester are connected to form an integrated system. The power management unit then connects to the energy storage (e.g. battery or capacitor) to store/recharge and distribute the energy to the other components of the capsule. Alternatively, the power management unit might be connected only to the batter and harvester, while all of the other components needing power connect directly to the battery as well.

Figure 14:
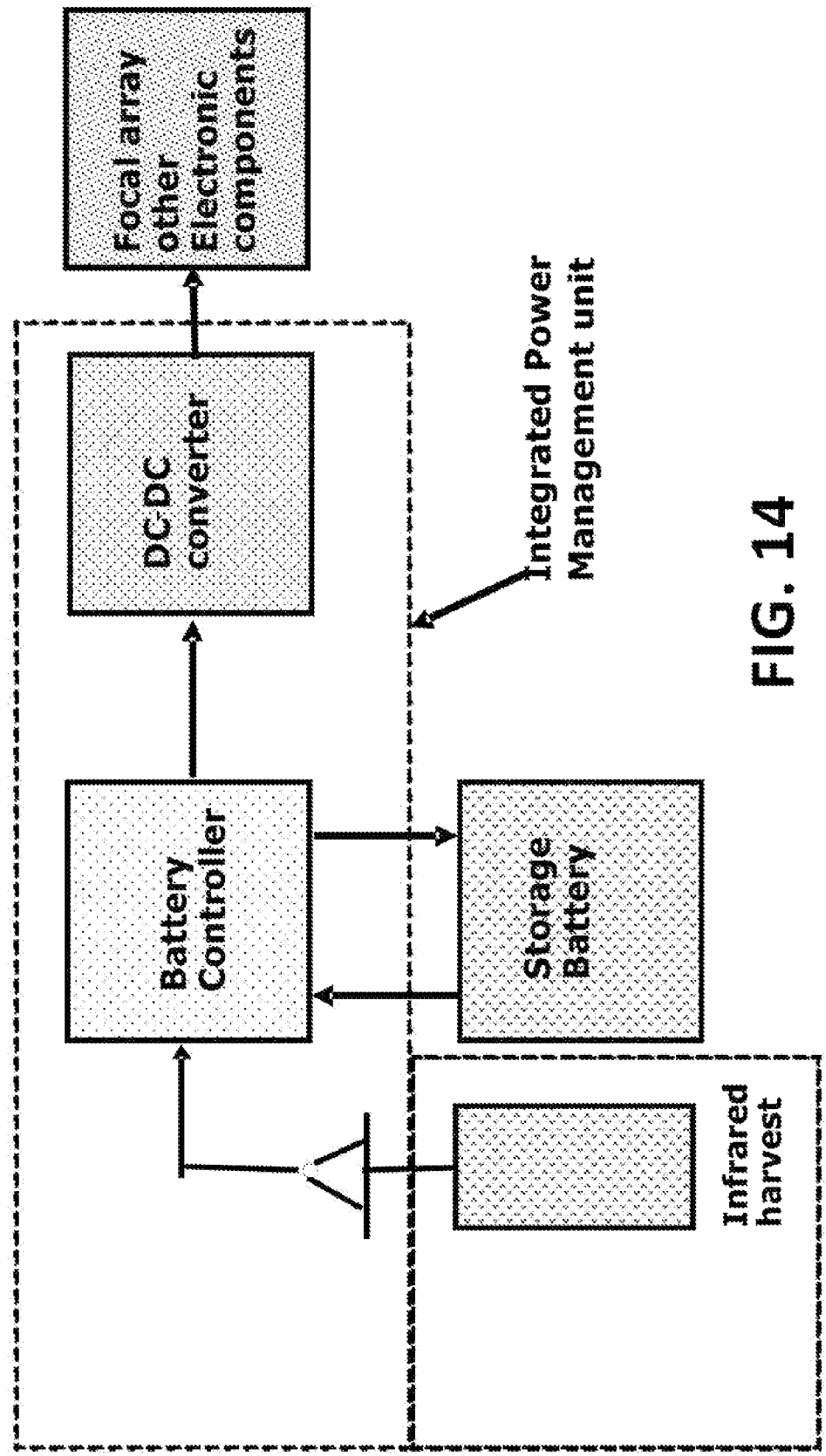
FIG. 14 is a schematic showing details of one possible arrangement of components, according to this invention.

FIG. 14 shows an alternate schematic for a method of connecting the components, according to this invention. In this embodiment, the integrated power unit comprises an energy harvester, a battery controller, and a DC-DC converter. The harvester supplies power to the energy storage (e.g. capacitor or battery) controller, which is connected to the DC-DC converter and to an external battery. The DC-DC converter is connected to the external focal array and communication components. All components as shown in FIG. 14, can also be made to sicglec chip, sizes of 1 to 5 sq. mm with thickness of less than 1 mm using CMOS technology.

FIGS. 13 and 14 are meant to serve as examples for how to connect the various components, and are not intended to be limiting. Other obvious variations would occur to a person skilled in the art.

According to this invention, the energy harvester can be structured many different ways. The device is structured as shown in FIG. 15i. The device is built on substrate 200, and consists of semiconductor layers 202 and 204. Those layers are doped opposite (either 202 is p-doped and 204 is n-doped, or vice versa). Additional layers of p or n doped material can also be inserted, or an intrinsic layer to form a p-i-n junction (not shown in here). Although pn-junctions and pin-junctions are favorable, other types of junctions are possible as well (not shown). For example, the device might utilize Schottkey-junctions, nBn, nBP, pB-i-n structures, quantum wells, quantum dots, or a combination. Electrical contacts 206 and 210 are formed such that each contact connects with a different semiconductor layer, and they are electrically insulated from each other with passivation material 208. Substrate 200 can be left as a support layer, doped to be part of the junction, etched out, or it can act as a power management system if formed from an integrated circuit is made on the substrate. If the integrated circuit (may make to power management system) is used as the substrate for energy harvester, then the harvester is fully integrated with the power management system, and external connection is unnecessary. If the integrated circuit (part of the power management unit) is not integrated into the harvester, then the harvester must be connected externally to the power management unit. FIG. 16A shows how the power management unit 212 would be connected to the energy harvester through use of indium bumps 214. The electrodes 216 in power management unit connects the energy harvester to other component such as image sensor and light emitter (if any), and also to the signal processing circuit for transmission (not shown here). Other integrated circuit for image sensor and also for the transmission all could be also integrated into one circuit (not shown here), according to this invention. FIG. 16B is an alternate embodiment according to this invention, wherein all numerals as explained in FIG. 15A, represents the same parts, so that repeated explanation is omitted here. Only difference is that the hybrid integration can also be hybridly connected to other integrated circuit, and or image sensor through the bumps 214, placed in other side of power management unit 212.

The preferred embodiment utilizes primarily HgCdTe, as an example, wherein HgCdTe is manufactured on an undoped silicon substrate 200 with a deposited layer of CdTe (not shown). The CdTe is a buffer layer to reduce stress between the silicon substrate and HgCdTe substrate, and can be doped or not. Doping with iodine creates n-type HgCdTe as the first layer 202. Doping with arsenic creates the p-type HgCdTe on top, 204. Metal Ohmic contacts 206 and 210 are made to the n-type and p-type devices on the top side, insulated from each other with passivation layer 208. Illumination is from the bottom silicon side. All infrared wavelengths between 1 .mu.m and greater than 10 .mu.m will pass through the silicon CdTe substrate. Up to 1 .mu.m of wavelength energy does not pass to the HgCdTe since it is absorbed by the CdTe and also Si substrate. This configuration creates a pn-junction sitting on top of a Silicon substrate, but many other configurations can be used instead. For example, pin-junctions, Schottkey junctions, quantum wells, quantum dot junctions, nBn detectors, or a combination. Additionally, the p-layer and n-layer need not be configured in the manner that is pictured. The layers could be easily reversed, and they need not be single layers.

Figure 15:
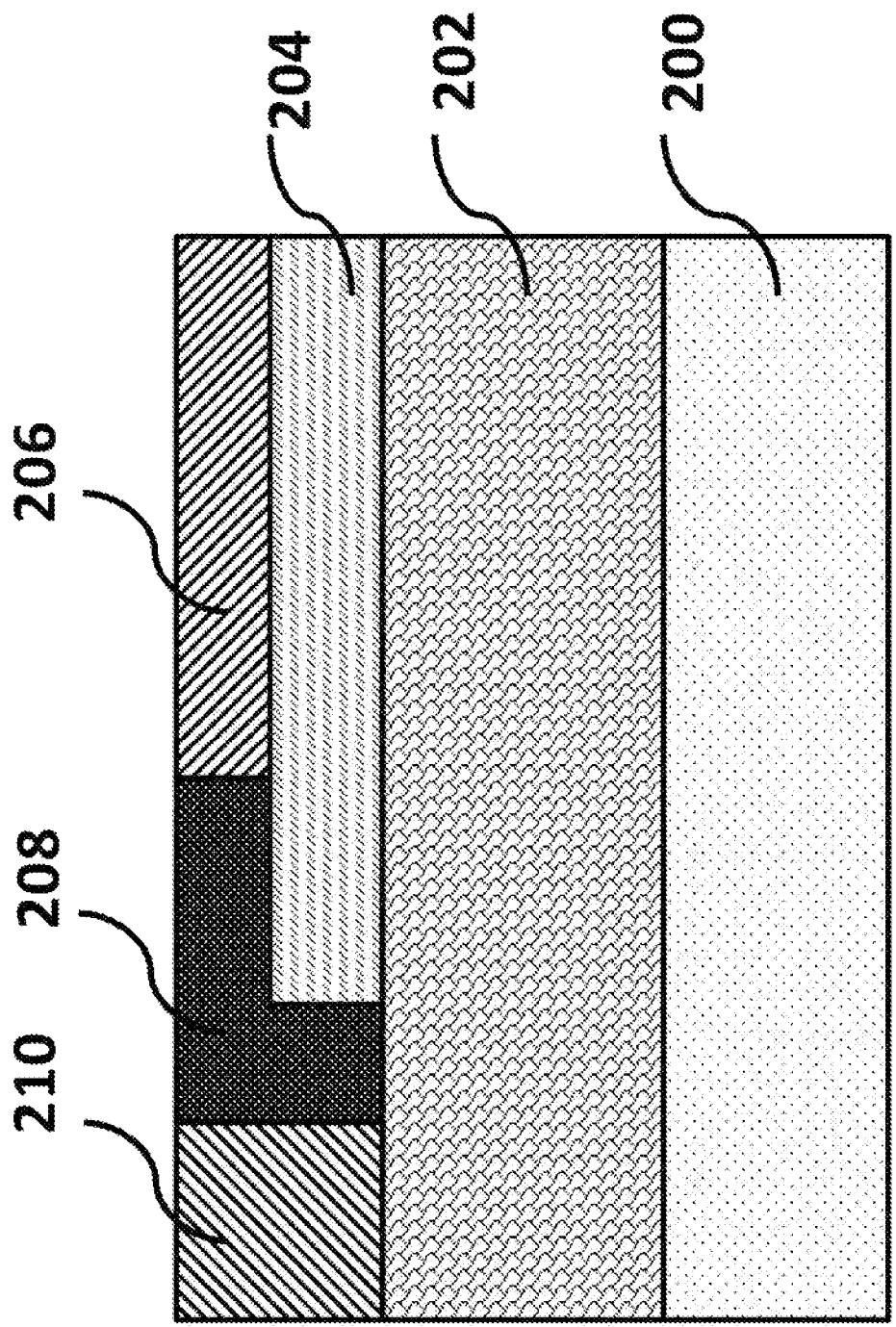
FIG. 15 is schematic showing the cross-sectional view of the energy harvester as a single element, according to this invention.
Figure 16A:
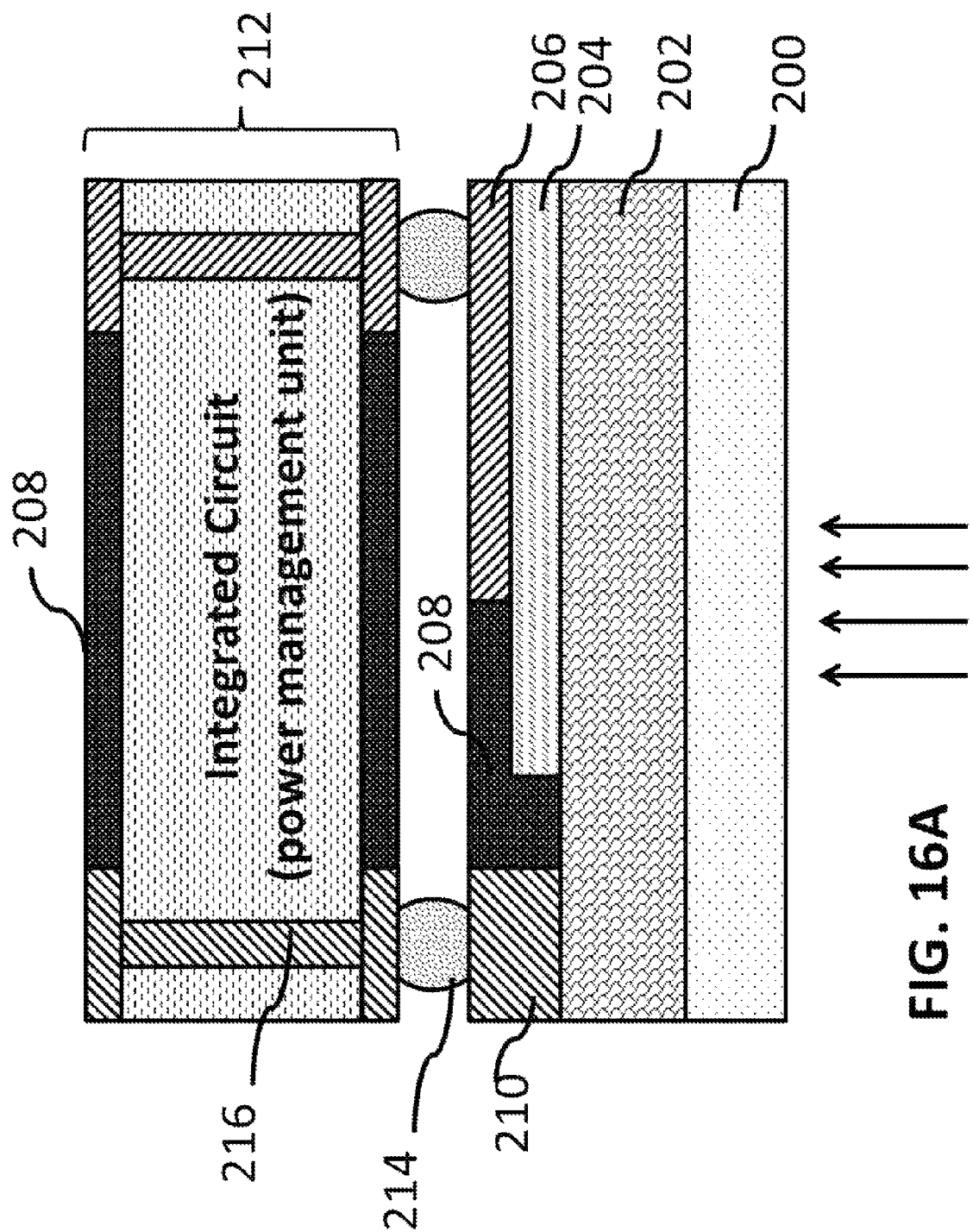
FIG. 16 are the schematics showing the embodiment of FIG. 15 externally connected to a power management unit through the use of indium bumps having connection: (A) one side and (B) both side with bumps, according to this invention.
Figure 16B:
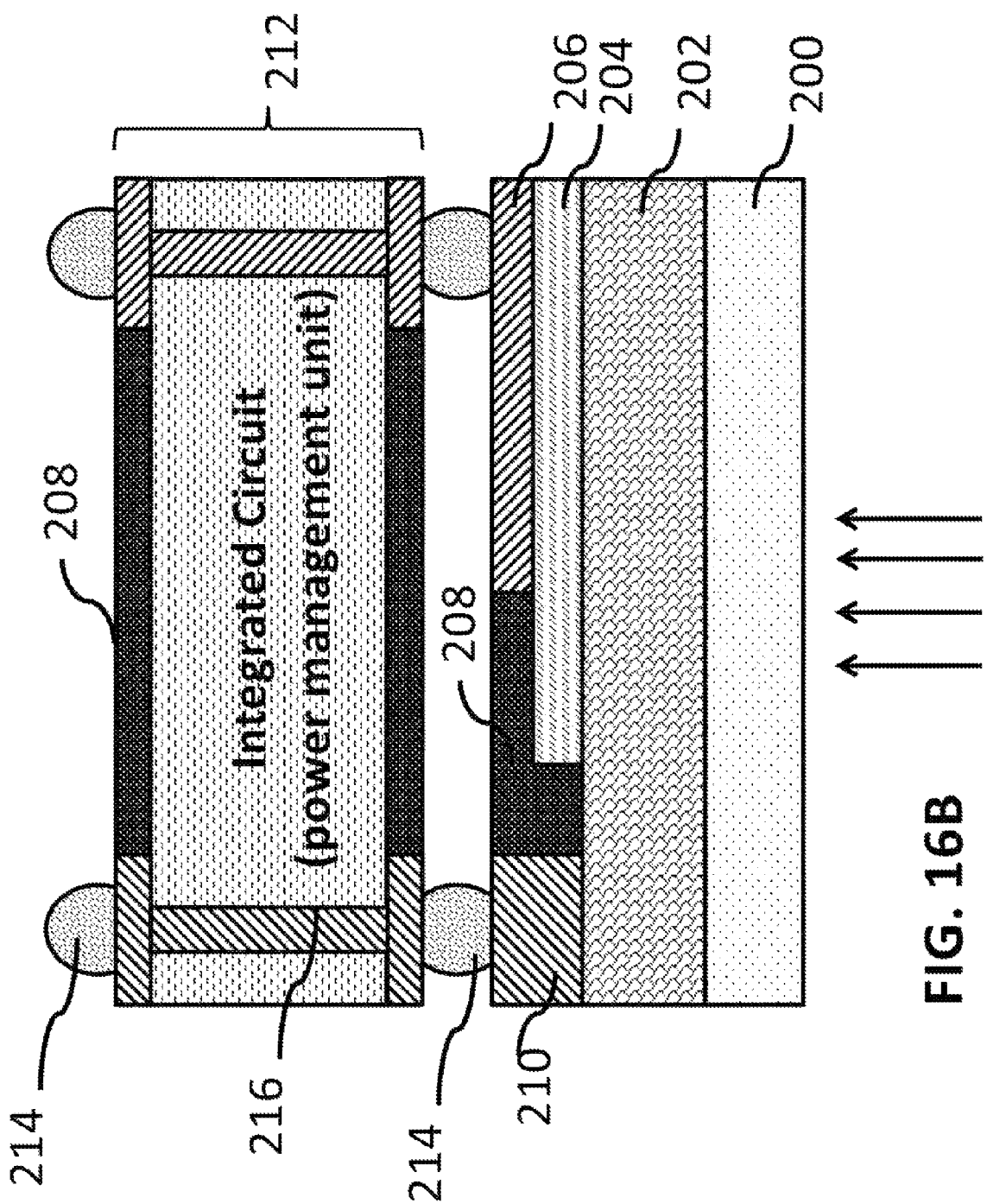

FIG. 15. shows the structure of a single diode (energy harvester). It might alternatively be placed in an array, or in combination with more diodes. The number of diodes in parallel or series will depend on desired current and voltage. The voltage in the case of the capsule harvesting structure will be above 4 to 5 volts to compensate for drop across the protection diode and to give more headroom to the power management unit.

Figure 17A:
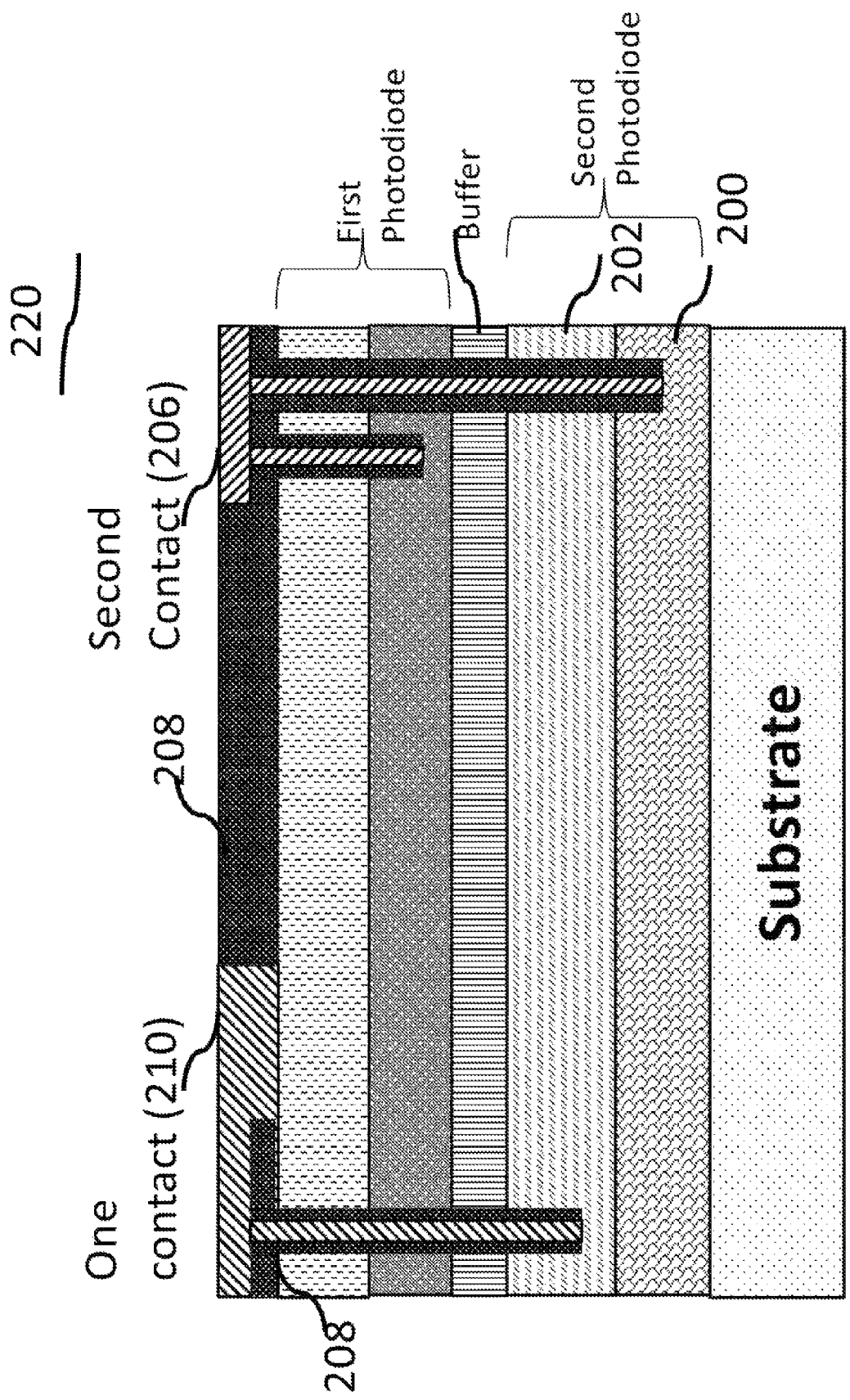
FIG. 17A is an alternate embodiment of the energy harvester, wherein two diodes are stacked on top of one another and connected/separated by a buffer layer, according to this invention.

FIG. 17A shows such a configuration for energy harvester 220, where two diodes are connected in series on the same wafer, according to this invention wherein same numerals represent the similar parts, as explained in FIG. 15 and FIG.

Figure 17B:
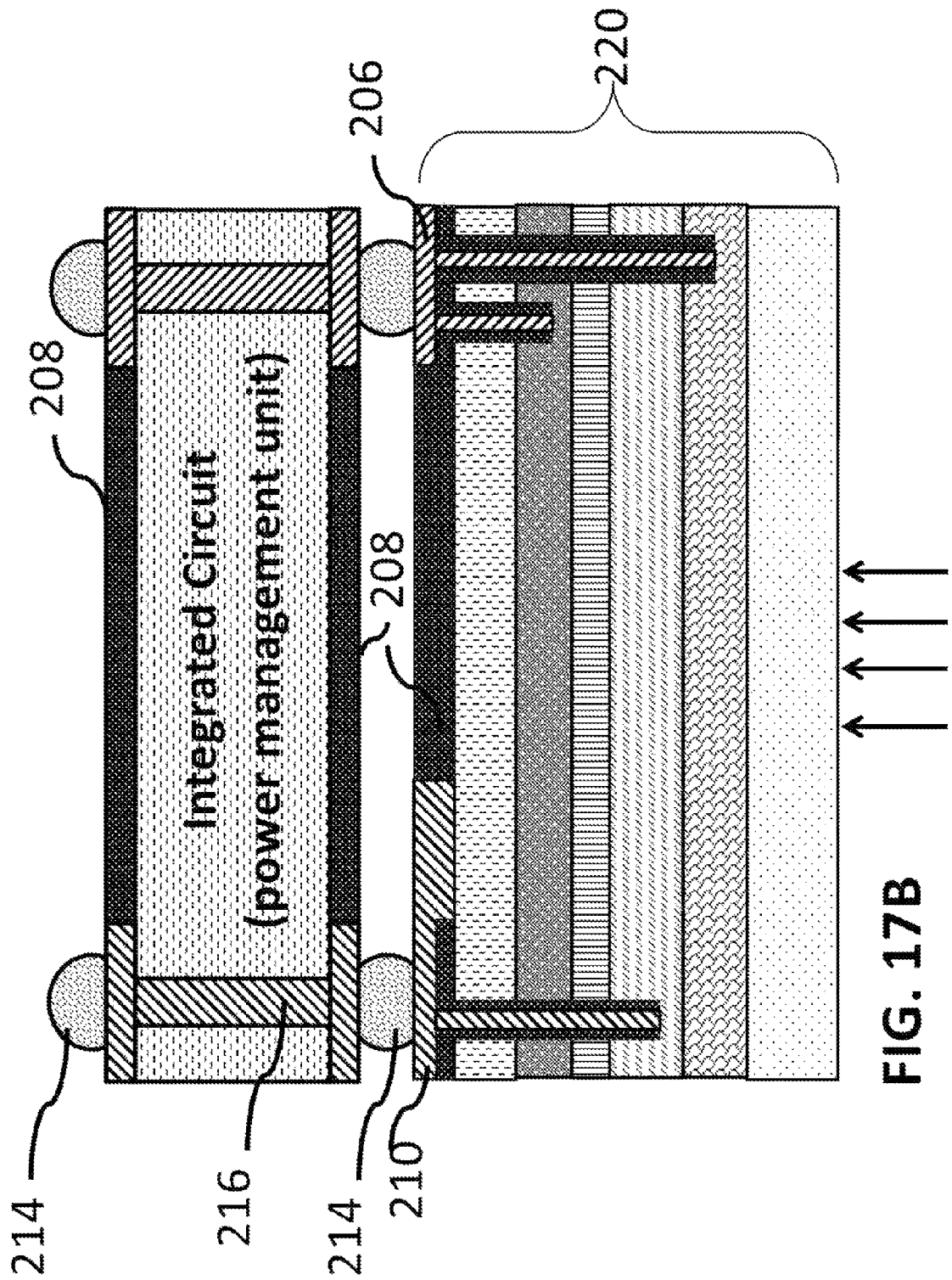
FIG. 17B shows the device of FIG. 17A externally connected to a power management unit through the use of indium bumps, according to this invention.

16, so that repeated explanation is omitted here. Any number of diodes can be connected in series and in parallel, and this figure is intended only as an example, not a limitation. When multiple such junctions are used, they can be formed from the same materials (HgCdTe) or different ones. If different materials are used within the same wafer, a buffer layer (or several) might be required in order to minimize lattice mismatch. If the diodes forming energy harvester 220, are connected through Indium bumps instead, as illustrated in another embodiment, as shown FIG. 17B, according to this invention, where buffer layers are not necessary.

Figure 18A:
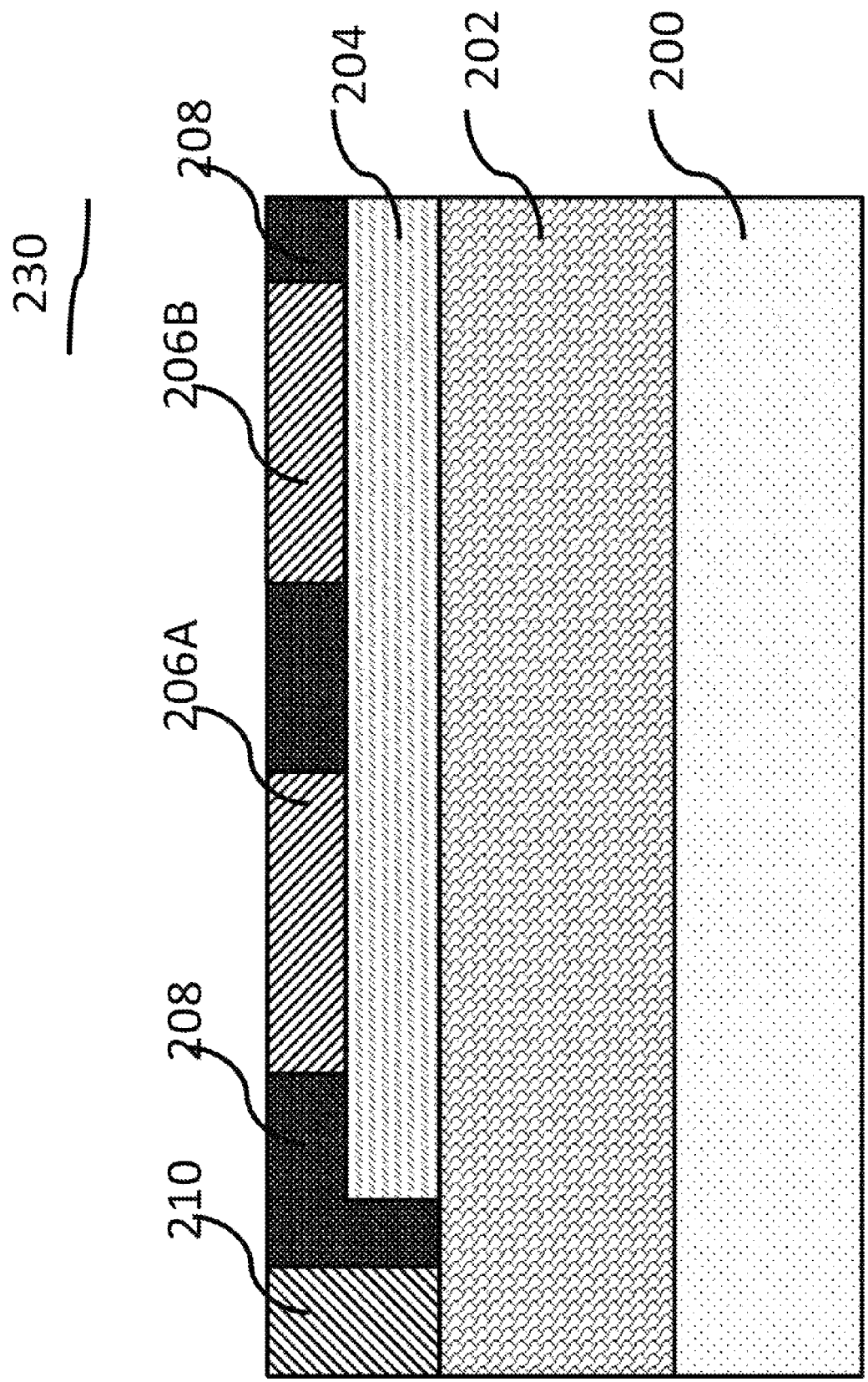
FIG. 18A is an alternate embodiment of the energy harvester, wherein more than one harvester element are placed side by side monolithically to make a energy harvester, according to this invention.
Figure 18B:
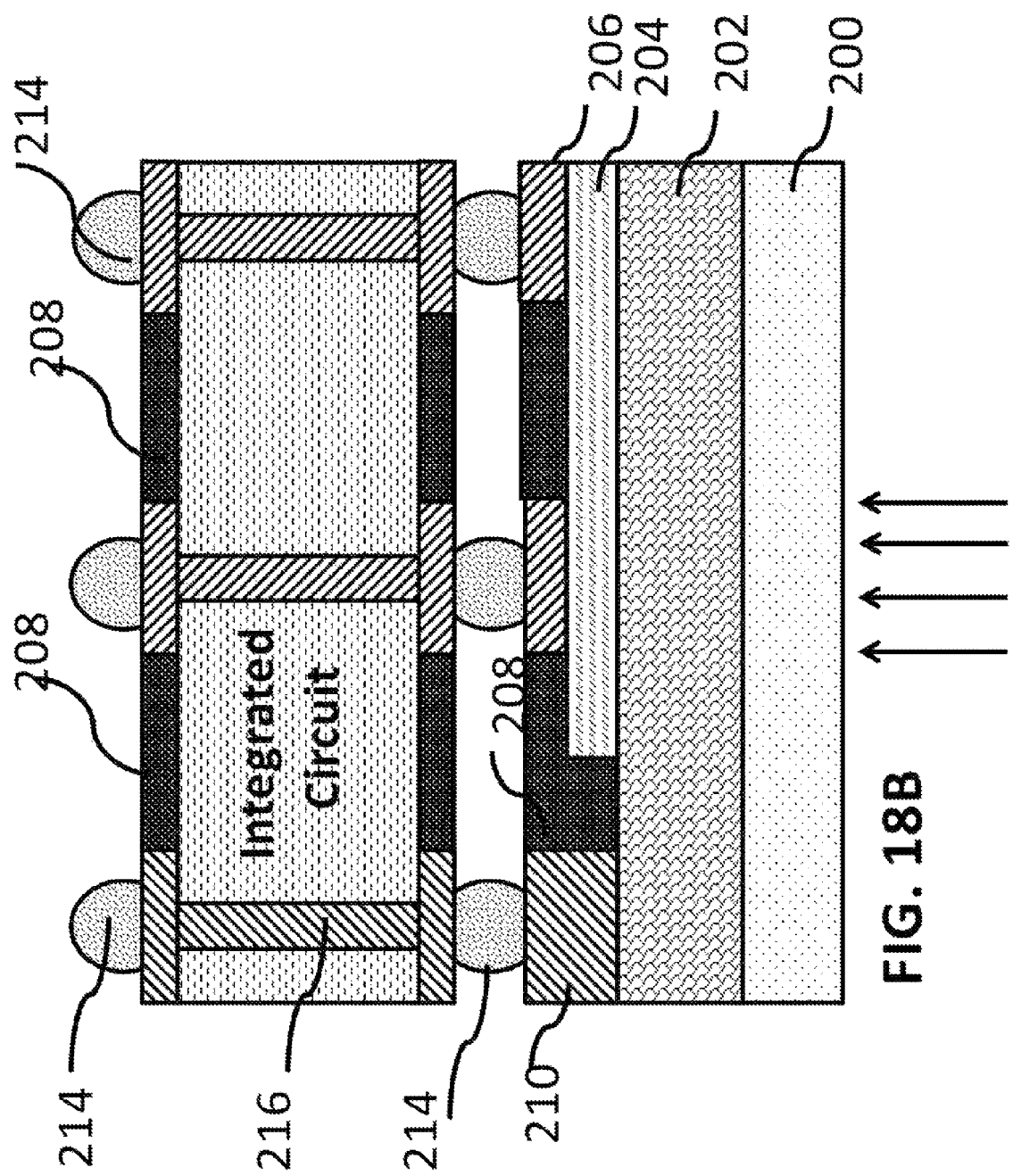
FIG. 18B shows the device from FIG. 18A externally connected to a power management unit through the use of indium bumps, according to this invention.

FIG. 18A shows the single-diode element for energy harvester as placed in an array 230 according to this invention wherein same numerals represent the similar parts, so that repeated explanation is omitted here. To achieve this, the harvester element might be formed separately and then connected, or they can be formed on the same wafer by forming multiple contacts for one semiconductor layer to form the harvester 230, while keeping one common contact for the other semiconductor layer. Alternatively, if placed in an array, each pixel need not be identical. Each harvester element comprising different types of diodes or different material types can also be utilized in order to expand the spectrum absorbed. FIG. 18B shows how such an array might be connected to an power management integrated circuit unit in much the same way as was shown in FIGS. 16B, and 17B The CMOS power management unit can be connected to the energy harvester in a number of ways. The simplest is to connect it to the ohmic contacts by way of Indium "bumps." Alternatively, the power management circuit can be integrated directly into a Silicon substrate, which the energy harvester is then formed on. In this way, the power management unit and energy harvester are both contained on the same wafer, and additional connection is not needed. Alternatively, if multiple diodes connected in series or parallel are being used, the power management unit might be integrated into one or more diodes, and then another (or multiple) diode is connected to the integrated system through Indium bumps.

As can be seen, the energy harvester structure is incredibly variable, depending on the specific needs of the structure being used. Once formed, the harvester and power management unit can also be further thinned in order to save space within the capsule. Preferably the combined energy harvester and power management unit will be less than 150 micrometers thin, but the preferred size can vary depending on placement and space available. An advantage of thinning out the Silicon substrate is reducing absorption of light in the spectrum of interest.

The focal array lens and infrared lens can alternatively be integrated directly into the shell of the capsule. Typically capsules are formed from clear plastic, but they might instead be formed from materials appropriate for use as lenses and then designed in such a way as to concentrate light on the focal array or energy harvesting device, or both.

As alternatives to the above preferred embodiment, the capsule according to this invention, can be formed from many different materials, and can be configured to absorb in different wavelengths. For example, the light emitter (e.g. LED) is only needed when imaging within the visible spectrum. However, the focal array can also be formed from materials which allow for non-visible imaging, such as IR. If this is done, then the either light emitter sensing that IR wavelengths, or nor light emitter are not necessary. In the case of capsule without light emitter, the IR image sensor is used which provide thermal imaging when capsule passes through the GI.

The light emitter is the main source of power draw within the capsule, so eliminating them allows for use of a smaller energy storage (e.g. battery), or even elimination of the energy storage altogether. With this in mind, many more options open up. The capsule can be made smaller and easier to swallow, or the extra space can be used for additional features, such as tissue sampling or pH testing. Alternatively, the extra space can be used for energy harvesters which are bigger, which opens the possibility to use the alternative harvesters mentioned previously. Although these alternatives are currently not as effective as the blackbody radiation harvester, they may be preferable in some embodiments due to cost of manufacturing or other factors.

Along a similar idea, the imaging focal array might utilize a combination of visible imaging and UV or IR imaging. In this case, some light from an light emitter might be needed, but not as much as if the focal array is purely visible imaging. In this case, the battery can be reduced but likely not eliminated altogether.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments is not intended to limit their scope. Although the invention has been described with respect to specific embodiment for complete and clear disclosure, the appended claims are not to be thus limited but are to be construed as embodying all modification and alternative constructions that may be occurred to one skilled in the art which fairly fall within the basic teaching here is set forth. Although the invention has been described with respect to specific embodiment for complete and clear disclosure, the appended claims are not to be thus limited but are to be construed as embodying all modification and alternative constructions that may be occurred to one skilled in the art which fairly tall within the basic teaching here is set forth.

What is claimed is:

1. An autonomous, self-powering image detecting capsule system comprising:
    a capsule shell,
        wherein said capsule shell has an inner surface and an outer surface;
    a first energy harvester,
        wherein said energy harvester is designed to harvest energy-from infrared with wavelengths greater than 3.5 μm;
    a power management system,
        wherein said power management system controls electrical energy from the first energy harvester to the other components;
    an image sensor array,
        wherein said image sensor array is designed to sense infrared spectrums of radiation;
    at least one lens,
        wherein at least one said lens is designed to focus radiation onto said image sensor array;
    a transmitter; and
    an antenna,
        wherein either said antenna touches said inner surface or said antenna partially or completely covers said outer surface.

2. The image detecting capsule of claim 1, further comprising a second energy harvester, wherein second energy harvester is designed to harvest energy from surrounding vibration and movement.

3. The image detecting capsule of claim 1, wherein said first energy harvester is designed to harvest energy in the infrared spectrum at wavelengths greater than 3.5 µm and is housed inside said capsule shell.

4. The image detecting capsule of claim 1, wherein said first energy harvester is designed to either partially or completely cover and touch the outer or inner surface of said capsule shell, wherein said power management system is integrated and electrically connected to the said first energy harvester.

5. The image detecting capsule of claim 1, wherein said antenna is placed either on the inner surface of the capsule shell or on the outer surface of the capsule shell.

6. The image detecting capsule of claim 1, wherein further comprising of an additional lens wherein said additional lens is designed to focus radiation onto said first energy harvester.

7. The image detecting capsule of claim 1, wherein said first energy harvester further comprising a second lens, formed as a part of said capsule shell.

8. The image detecting capsule of claim 1, wherein said image sensor array is made either rigid or flexible, wherein said image sensor array is placed on said inner surface of said capsule shell.

9. The image detecting capsule of claim 1, wherein said first energy harvester is designed to harvest energy in the infrared spectrum and comprises at least one HgCdTe-based energy harvester formed on a silicon substrate, wherein said HgCdTe-based energy harvester utilizes a pn-junction, pin-junction, Schottky junction, quantum well, quantum dot junction, nBn detector, or a combination thereof, and wherein the image sensor array is designed to sense broad spectrum of radiation.

10. The image detecting capsule of claim 9, wherein said power management system is an integrated circuit, and the integrated circuit is either formed monolithically on the same substrate the first energy harvester is connected to, or separately formed and electrically connected to the energy harvester.

11. The image detecting capsule of claim 1, further comprising an energy storage unit selected from a group consisting of capacitor and battery.

12. An autonomous self-powering powering image detecting capsule comprising:
a capsule shell,
    wherein said capsule shell has an inner surface and an outer surface;
a first energy harvester,
    wherein said first energy harvester is designed to harvest energy from the infrared wavelengths greater than 3.5 µm;
a power management system;
an image sensor array,
    wherein said image sensor array is designed to sense in the visible spectrum;
at least one lens,
    wherein at least one said at least one lens is designed and placed to focus light on said image sensor array;
at least one light emitter;
a battery;
a transmitter;
and an antenna;
    wherein either said antenna touches said inner surface or said antenna partially or completely covers said outer surface;
    wherein said power management system is electrically connected to the said first energy harvester and said battery, and controls the electrical current from the said first energy harvester to the said battery.

13. The image detecting capsule of claim 12, wherein said first energy harvester partially or completely covers and touches the outer surface of said capsule shell and said power management system is integrated into the said first energy harvester.

14. The image detecting capsule of claim 12, wherein said first energy harvester is made from semiconductor materials.

15. The image detecting capsule of claim 12, wherein said at least one lens is flexible type and formed as a part of said capsule shell.

16. The image detecting capsule of claim 12 further comprising a second energy harvester, designed to harvest energy from surrounding vibration and motion.

* * * * *